United States Patent
Allison et al.

(10) Patent No.: US 6,413,218 B1
(45) Date of Patent: Jul. 2, 2002

(54) MEDICAL DIAGNOSTIC ULTRASOUND IMAGING SYSTEM AND METHOD FOR DETERMINING AN ACOUSTIC OUTPUT PARAMETER OF A TRANSMITTED ULTRASONIC BEAM

(75) Inventors: John W. Allison, Los Altos; Lewis J. Thomas, Palo Alto; Sriram Krishnan, San Jose; Gregory L. Holley, Mountain View, all of CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/501,443

(22) Filed: Feb. 10, 2000

(51) Int. Cl.$^7$ ................................................ A61B 8/00
(52) U.S. Cl. ..................................................... 600/443
(58) Field of Search .............................. 600/437, 443, 600/447, 458

(56) References Cited

U.S. PATENT DOCUMENTS

| | | | | |
|---|---|---|---|---|
| 5,113,706 A | * | 5/1992 | Pittaro .......................... | 600/447 |
| 5,313,947 A | * | 5/1994 | Micco .......................... | 600/455 |
| 5,331,964 A | * | 7/1994 | Trahey et al. ................ | 600/447 |
| 5,357,962 A | * | 10/1994 | Green .......................... | 600/443 |
| 5,482,046 A | * | 1/1996 | Deitrich ....................... | 600/458 |
| 5,509,413 A | * | 4/1996 | Akama et al. ............... | 600/458 |
| 5,551,434 A | * | 9/1996 | Iinuma ......................... | 600/455 |
| 5,634,465 A | | 6/1997 | Schmiesing et al. | |
| 5,640,959 A | * | 6/1997 | Hara et al. .................... | 600/447 |
| 5,709,209 A | * | 1/1998 | Friemel et al. ............... | 600/443 |
| 5,882,306 A | * | 3/1999 | Ramamurthy et al. ....... | 600/440 |
| 5,891,040 A | * | 4/1999 | Grenon et al. ............... | 600/455 |
| 6,036,643 A | | 3/2000 | Criton et al. | |
| 6,077,225 A | * | 6/2000 | Brock-Fisher ............... | 600/439 |
| 6,080,107 A | * | 6/2000 | Poland ......................... | 600/458 |
| 6,123,670 A | * | 9/2000 | Mo ............................... | 600/447 |
| 6,146,329 A | * | 11/2000 | Hayakawa .................... | 600/443 |
| 6,146,330 A | * | 11/2000 | Tujino et al. ................. | 600/443 |
| 6,149,597 A | * | 11/2000 | Kamiyama .................... | 600/458 |
| 6,200,267 B1 | * | 3/2001 | Burke ........................... | 600/443 |
| 6,210,335 B1 | * | 4/2001 | Miller .......................... | 600/454 |
| 6,217,516 B1 | * | 4/2001 | Poland et al. ................ | 600/437 |
| 6,245,019 B1 | * | 6/2001 | Kamiyama ................... | 600/458 |
| 6,258,033 B1 | * | 7/2001 | Grenon ........................ | 600/458 |

OTHER PUBLICATIONS

Melton, H.E. et al "Rational–Gain–Compensation for Attenuation In Ultrasonic Cardiac Imaging", 1981 IEEE Symposium pp. 601–611.*

AIUM –NEMA "Standards for Real–Tuime Display of Thermal and Mechanical Acoustic Output Indices on Diagnostic Ultrasound Equipment" 1998.*

AIUM–NEMA "Acoustic Output Measurement Standard for Diagnostic Ultrasound Equipment" 1998.*

* cited by examiner

*Primary Examiner*—Francis J. Jaworski
(74) *Attorney, Agent, or Firm*—Brinks Hofer Gilson & Lione

(57) ABSTRACT

The preferred embodiments described herein provide a medical diagnostic ultrasound imaging system and method for determining an acoustic output parameter of a transmitted ultrasonic beam. In one preferred embodiment, the ultrasound system determines an acoustic output parameter of a transmitted ultrasonic beam in a user-selected region. In another preferred embodiment, the ultrasound system achieves a specified acoustic output parameter of a transmitted ultrasonic beam in a selected region by automatically adjusting an operating parameter of the ultrasound imaging system. In yet another preferred embodiment, a region is selected in the ultrasound image that does not contain a peak acoustic output parameter of a transmitted ultrasonic beam. The system then determines an acoustic output parameter of the transmitted ultrasonic beam in that region and provides an indication of the determined acoustic output parameter.

60 Claims, 3 Drawing Sheets

MEDICAL DIAGNOSTIC ULTRASOUND IMAGING SYSTEM AND METHOD FOR DETERMINING AN ACOUSTIC OUTPUT PARAMETER OF A TRANSMITTED ULTRASONIC BEAM

BACKGROUND

The Federal Drug Administration requires that the peak rarefractional pressure of an ultrasonic beam entering a patient be below a specified level. To ensure this requirement is met, medical diagnostic ultrasound imaging systems often display the mechanical index, which is related to the peak acoustic pressure in the imaging field. The displayed mechanical index can also be used to set-up and conduct a contrast imaging examination. The non-linear response (harmonics or destruction) of contrast agents is dependent, in part, on the acoustic pressure of an ultrasonic wave. If a non-linear response is not desired, a user of the ultrasound system can reduce the transmit power, for example, to reduce the displayed mechanical index to a level that will minimize undesired responses in the contrast agent. However, the displayed mechanical index may not be related to the location in the imaging field where the contrast agent is present. Accordingly, the use of the displayed mechanical index is often only a crude measure of the relevant pressure and can result in sub-optimal imaging conditions. For example, a user may reduce the transmit power to a level lower than needed to avoid a non-linear response from the contrast agent, thereby making an unnecessary sacrifice in image quality. Also, with the current approach, multiple injections of contrast agent into a patient may be needed to optimize the imaging procedure. Additionally, the spatial ambiguity associated with the displayed mechanical index can result in error when comparing the response of contrast agent from two regions of interest.

There is a need, therefore, for a medical diagnostic ultrasonic imaging system and method that overcomes the disadvantages described above.

SUMMARY

The present invention is defined by the following claims, and nothing in this section should be taken as a limitation on those claims.

By way of introduction, the preferred embodiments described below provide a medical diagnostic ultrasound imaging system and method for determining an acoustic output parameter of a transmitted ultrasonic beam. In one preferred embodiment, the ultrasound system determines an acoustic output parameter of a transmitted ultrasonic beam in a user-selected region. In another preferred embodiment, the ultrasound system achieves a specified acoustic output parameter of a transmitted ultrasonic beam in a selected region by automatically adjusting an operating parameter of the ultrasound imaging system. In yet another preferred embodiment, a region is selected in the ultrasound image that does not contain a peak acoustic output parameter of a transmitted ultrasonic beam. The system then determines an acoustic output parameter of the transmitted ultrasonic beam in that region and provides an indication of the determined acoustic output parameter.

The preferred embodiments will now be described with reference to the attached drawings.

DETAILED DESCRIPTION OF THE PRESENTLY PREFERRED EMBODIMENTS

Figure 1:
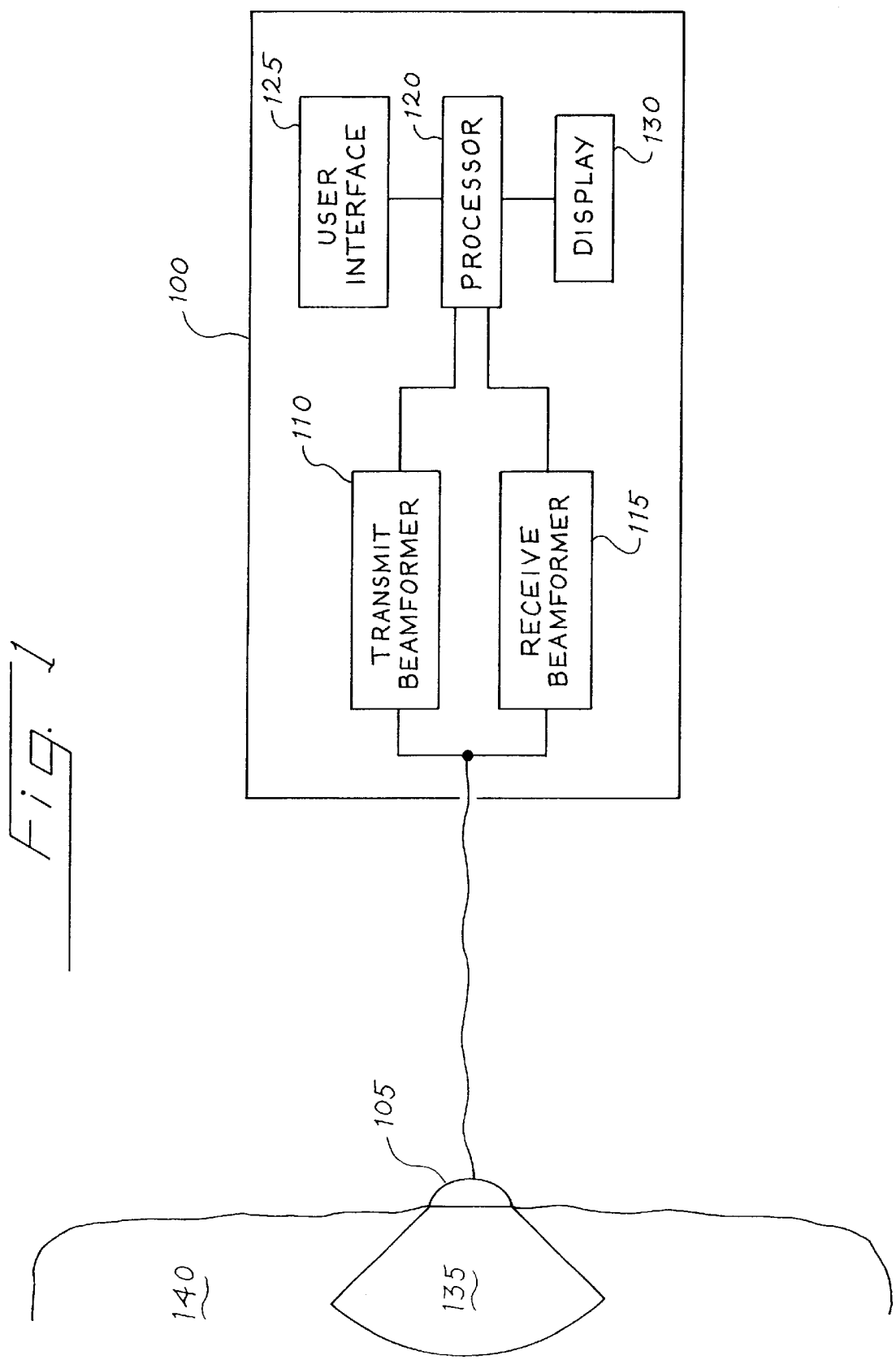
FIG. 1 is a block diagram of a medical diagnostic ultrasound imaging system of a presently preferred embodiment.

Turning now to the figures, FIG. 1 is a block diagram of a medical diagnostic ultrasound imaging system 100 and transducer 105 of a presently preferred embodiment. The ultrasound system 100 can be used with any suitable imaging mode (e.g., B-mode imaging, Doppler imaging, tissue harmonic imaging, contrast agent harmonic imaging, etc.), and the transducer 105 can be of any type (e.g., 1D, 1.5D, plano-concave, single element, phased-array, etc.). The transducer 105 is coupled with a transmit beamformer 110 and a receive beamformer 115. As used herein, the term "coupled with" means directly coupled with or indirectly coupled with through one or more components.

The beamformers 110, 115 are each coupled with a processor 120, which is coupled with a user interface 125 and a display 130. The term "processor" broadly refers to the appropriate hardware and/or software components of the ultrasound system 100 that can be used to implement the preferred embodiments described herein. It should be understood that any appropriate hardware (analog or digital) or software can be used and that the embodiments described herein can be implemented exclusively with hardware. Further, the processor 120 can be separate from or combined with (in part or in whole) other processors of the ultrasound system 100 (including attendant processors), which are not shown in FIG. 1 for simplicity.

In operation, the processor 120 causes the transmit beamformer 110 to apply a voltage to the transducer 105 to cause it to vibrate and emit an ultrasonic beam 135 into an object 140, such as human tissue (i.e., a patient's body). Ultrasonic energy reflected from the body impinges on the transducer 105, and the resulting voltages created by the transducer 105 are received by the receive beamformer 115. The processor 120 processes the sensed voltages to create an ultrasound image associated with the reflected signals and displays the image on the display 130. Typically, several ultrasonic beams are used to generate an ultrasound image. The user interface 125 can be used, for example, to adjust parameters used in the transmit, receive, and display operations. It should be noted that the ultrasound imaging system 100 can comprise additional components.

The ultrasound system 100 is operative to perform one or more operations relating to the determination and/or calibration of an acoustic output parameter of a transmitted ultrasonic beam, as described below. As used herein, the term "acoustic output parameter of a transmitted ultrasonic beam" is broadly meant to cover any acoustic output parameter of an ultrasonic beam emitted from a transducer of a medical diagnostic ultrasound imaging system. It is preferred that the acoustic output parameter be an index of thermal and/or mechanical acoustic output and that the acoustic output parameter be able to affect contrast agent modification (e.g., that the acoustic output parameter be able to cause a non-linear response in contrast agent). Indices of thermal acoustic output include, but are not limited to, acoustic power, acoustic energy, thermal index (TI), bone thermal index (TIB), cranial bone thermal index (TIC), soft tissue thermal index (TIS), and pulse intensity integral (PII). Indices of mechanical acoustic output include, but are not limited to, pressure (compressional or rarefractional), instantaneous spatial peak temporal average (ISPTA), and mechanical index, which is conventionally defined as the peak rarefractional pressure of the transmitted ultrasonic beam divided by the square root of the transmit frequency.

Figure 2:
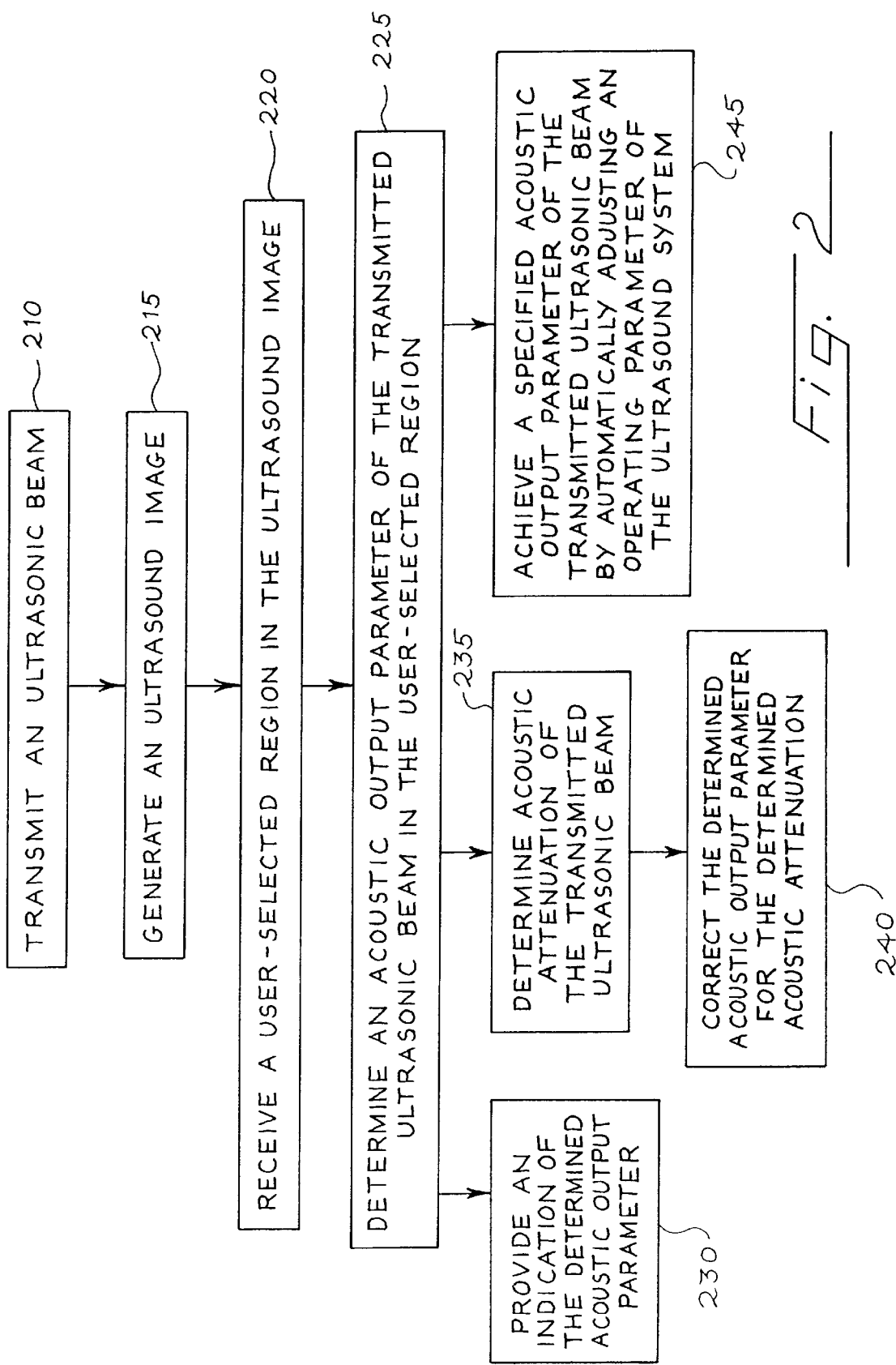
FIG. 2 is a flow chart of a method of a presently preferred embodiment for determining an acoustic output parameter of a transmitted ultrasonic beam in a user-selected region in an ultrasound image.
Figure 3:
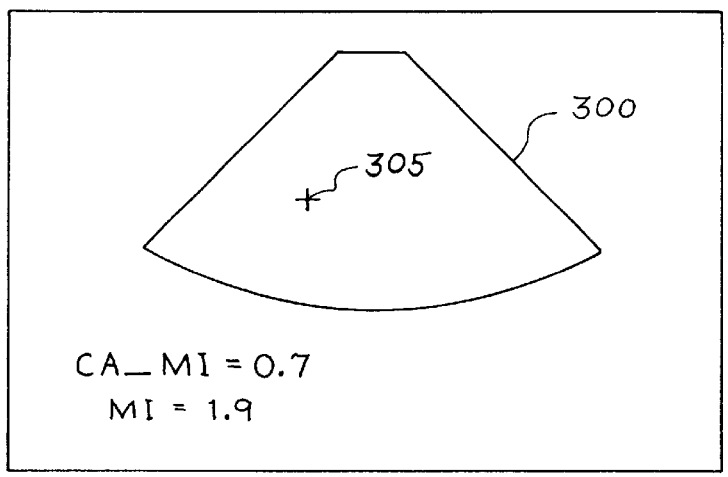
FIG. 3 is an illustration of an ultrasound image illustrating the preferred method of FIG. 2 in which the user-selected region is a point.
Figure 4:
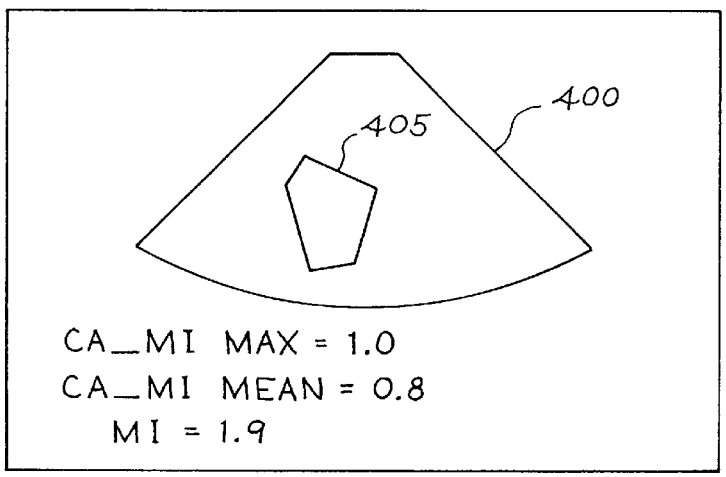
FIG. 4 is an illustration of an ultrasound image illustrating the preferred method of FIG. 2 in which the user-selected region comprises a plurality of points.
Figure 5:
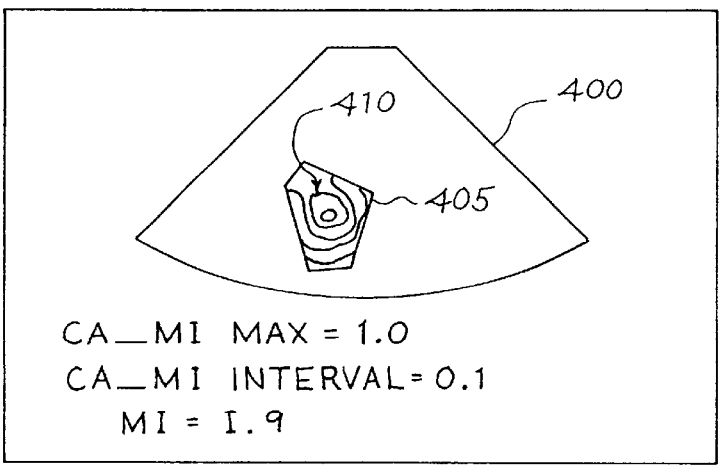
FIG. 5 is an illustration of an ultrasound image illustrating the preferred method of FIG. 2 in which an isobar representation is used to indicate the determined acoustic output parameters in the user-selected region.

The ultrasound system 100 can be used in a method for determining an acoustic output parameter of a transmitted ultrasonic beam in a user-selected region in an ultrasound image, as shown in the flow chart 200 of FIG. 2. FIGS. 3–5 are ultrasound images that will aid in the illustration of this method. First, an ultrasonic beam is transmitted from the transducer 105 (act 210), and then the ultrasound system 100 generates an ultrasound image 300, shown in FIG. 3 (act 215). Next, the ultrasound system 100 receives a selection of a region in the ultrasound image from a user (act 220). As used herein, a "region" can be a single point or a plurality of points, such as when the region is defined by a line or an arbitrary or predefined shape. For example, in the ultrasound image 300 of FIG. 3, the region is a point indicated by a caliper 305, while in the ultrasound image 400 of FIGS. 4 and 5, the region 405 is a plurality of points enclosed by a pentagonal shape. It should be noted that a "region" can also refer to a subset of points in a line or enclosed by an arbitrary or predefined shape. For example, a "region" can be one, some or all of the points on a line or enclosed by a shape. The user can select a region, for example, by interacting with the user interface 125 (e.g., a trackball, mouse, keyboard, touchpad, touchscreen, voice recognizer, etc.) to position a cursor or other visual indicator (such as caliper 305) on the ultrasound image displayed on the display 130. If the underlying tissue being imaged is in motion, the cursor can be repositioned automatically from frame to frame to track the original location in the tissue.

After the user-selected region is received by the ultrasound system 100, an acoustic output parameter of the transmitted ultrasonic beam in the user-selected region is determined (act 225). As noted above, a "region" can be a subset of points defined by a line or enclosed by an arbitrary or predefined shape. For example, in FIG. 4, the "region" in which the acoustic output parameter is determined can be one, some, or all of the points enclosed by the pentagonal shape 405. An acoustic output parameter can be "determined" by measurement, calculation, estimation, prediction, or any other suitable method. The following two documents, which are hereby incorporated by reference, describe a suitable method that can be used to determine parameters of the transmitted acoustic field: "Standard for Real-Time Display of Thermal and Mechanical Acoustic Output Indices on Diagnostic Ultrasound Equipment," Revision 1 (1998) and "Acoustic Output Measurement Standard for Diagnostic Ultrasound Equipment" (1998), both of which are published by American Institute of Ultrasound in Medicine and National Electrical Manufacturers Association. The hardware and/or software that is used to determine the acoustic output parameter of the transmitted ultrasonic beam can be the same as that used in conventional ultrasound systems to determine mechanical index. The difference here being that the acoustic output parameter is determined in the user-selected region instead of the fixed location of peak pressure. The act of determining can be done during acquisition or post-acquisition on captured frames or clips. For post-acquisition determination, it is preferred that the ultrasound system's operating conditions be recorded to aid in post-acquisition determination either by the ultrasound system 100 or by an external analysis-and-quantification system.

After the acoustic output parameter is determined, the ultrasound system 100 can provide an indication of the determined acoustic output parameter (act 230). The indication can take any suitable form including, but not limited to, a visual, aural, or tactile indication. The indication can be provided on the ultrasound system itself (such as when a visual indication is provided on the displayed image or on the system itself (e.g., via an LED)) or can be provided by a device external to the ultrasound system (such as when the indication is spoken via an external speaker). Of course, other methods of providing the indication can be used, such as with sound, light, or a tactile indicator when the determined acoustic output parameter is equal to, above, or below a threshold.

The displays of FIGS. 3–5 illustrate some of the various forms by which the determined acoustic output parameter can be indicated. In these figures, the acoustic output parameter is the pressure of the transmitted ultrasonic beam. The use of this specific acoustic output parameter is for illustration purposes only and is in no way intended to limit the scope of the claimed invention. To provide a useful comparison between the determined pressure and the mechanical index, it is preferred that the determined pressure be divided by the square root of the transmit frequency. In these figures, this quantity is referred to as the contrast agent mechanical index (CA_MI). In FIG. 3, the user-selected region is a single point, and the determined CA_MI is displayed with the image. As shown in FIG. 3, the mechanical index (MI) is also displayed. Although the mechanical index does not necessarily need to be displayed to practice these preferred embodiments, it may be preferred to display the mechanical index to comply with governmental regulations. Of course, multiple acoustic output parameters can be determined and displayed.

In FIG. 3, the user-selected region is a single point, and the provided indication is a single value associated with the single point. If the user-selected region is a plurality of points, the provided indication can be for one, some, or all of the points in the region, as shown in FIGS. 4 and 5. In FIGS. 4 and 5, the user-selected region comprises a plurality of points enclosed by a pentagonal shape 405. A distribution (e.g., maximum, minimum, mean, mode, variance) of the determined acoustic output parameters for the plurality of points can be determined and indicated. For example, in FIG. 4, the mean value of the determined acoustic output parameters is displayed (CA_MI MEAN), and in FIGS. 4 and 5, the maximum value is displayed (CA_MI MAX). The provided indication can also take the form of a one-, two-, or three-dimensional isobar or map (grayscale or color) to indicate a range of the determined acoustic output parameters in the user-selected region. For example, points or areas within the user-selected region can be indicated where the determined acoustic output parameter is equal to, above, or below a threshold. In FIG. 5, an isobar representation is used, and the pentagonal region 405 is filled with contour lines 410. FIG. 5 indicates the value of the maximum contour (CA_MI MAX=1.0) and the contour interval (CA_MI Interval=0.1).

There are several advantages associated with these preferred embodiments. For example, because the acoustic output parameter is determined at the user-selected region, there is no spatial ambiguity of where in the image the parameter is being determined, unlike the determination of mechanical index in conventional ultrasound systems. Also, these preferred embodiments can provide a description of spatial non-uniformity of acoustic output parameters and allow consistent optimization of acoustic output parameters across transducers, modes, frequencies, and imaging applications.

These preferred embodiments find additional advantages in contrast agent imaging applications. In contrast agent imaging, it is often preferred to limit the pressure (or other acoustic output parameters) of the transmitted ultrasonic beam to a value that will minimize undesired responses in the contrast agent. With these preferred embodiments, a user can select a region in the ultrasound image where contrast agent is or will be present (such as a ventricle of the heart) and can monitor the pressure of the transmitted beam in that region. With this feedback, the user can adjust operating parameters of the ultrasound system to achieve the desired level, thereby optimizing contrast agent response and removing or minimizing effects caused by non-uniform acoustic output parameters. As used herein, the term "operating parameters of the ultrasound system" is meant to broadly refer to any operating parameter that can be adjusted to affect an acoustic output parameter. Operating parameters include, but are not limited to, apodization, number of elements in the transmit aperture, focal range, transmit voltage, and time duration of the ultrasonic pulse.

In addition to improving quantification of contrast image data, these preferred embodiments can aid in analyzing contrast image data between studies and improve the reproducibility of contrast imaging examinations by recording the determined acoustic output parameters. Further, by determining an acoustic output parameter prior to the injection of contrast agent, the user can confirm that the desired acoustic output parameter is achieved before commencing a contrast protocol. This makes the examination more efficient and avoids injecting the patient with more contrast agent than is necessary for the examination. Similar advantages can be achieved in other imaging applications such as in the field of drug delivery by means of ultrasonic destruction of a drug-carrying vessel. For example, the preferred embodiments can aid in the determining of the rate of drug delivery and dosage.

In addition to or as an alternative to the user adjusting an operating parameter of the ultrasound system, the ultrasound system itself can automatically adjust operating parameters. For example, a user can specify or preset a target acoustic output parameter (such as pressure) for one or more points in the region for optimal contrast agent imaging. After the acoustic output parameter is determined, the ultrasound system can achieve the specified acoustic output parameter by automatically adjusting an operating parameter of the system (act 245).

There are several alternatives that can be employed with these preferred embodiments. In one alternate embodiment, instead of or in addition to the user manually selecting a region in the ultrasound image, the ultrasound imaging system can automatically select a region. For example, the ultrasound imaging system can select a region based on a default or user-specified point, image depth, or azimuthal transmit focus.

Another alternate embodiment relates to attenuation of the ultrasonic beam. Because of attenuation of the ultrasonic signal along the propagation path, the determined acoustic output parameter may not be accurate. To provide a more accurate determination, the ultrasound system 100 preferably determines acoustic attenuation of the transmitted ultrasonic beam (act 235) and adjusts/calibrates the determined acoustic output parameter for the determined acoustic attenuation to compensate for actual imaging conditions (act 240). To determine acoustic attenuation of the transmitted ultrasonic beam, data can be acquired along an acoustic line from the transducer 105 to the user-selected region, and an estimate of the attenuation coefficient along this acoustic line can be determined using a single firing or multiple firings along the line. Operating parameters (such as frequency and bandwidth) that vary between pulse firings along the line can be used to estimate the average attenuation along the line. One suitable technique for calculating attenuation is described in "Rational-Gain-Compensation for Attenuation in Cardiac Imaging," H. E. Melton, Jr. and D. J. Skorton, Proc. IEEE Symposium on Sonics and Ultrasonics, #81CH1689-9, pp. 607–611 (1981), which is hereby incorporated by reference. This technique identifies regions of the ultrasound image as depicting either tissue or blood by analyzing the echo brightness of the received beamformed signal. Tissue has high intensity echoes, and blood has virtually no echoes. Attenuation is calculated using typical parameters for blood and tissue.

Another calibration technique that can be used separate from or in addition to the acoustic attenuation calibration described above relates to in vivo measurement of an acoustic output parameter. A determined acoustic output parameter can be based on actual measurements and power management models for specific ultrasound system operating conditions assuming homogenous (ideal) imaging conditions. Clinical conditions frequently introduce inhomogeneities that cause the actual acoustic output parameter to be significantly different from the determined acoustic output parameter. An in vivo measure of the acoustic output parameter can be made by using a population of contrast agents consisting of one or more agents with different levels of non-linear response (e.g., destruction) as a function of an acoustic output parameter. As operating parameters change to increase the acoustic output parameter, the first onset of non-linear response indicates when the first non-linear threshold is achieved at a point of interest (a manually- or automatically-selected region). Subsequent non-linear responses can be observed with additional contrast agents in the population with varying non-linear thresholds. Single or multiple threshold levels can be used to calibrate the acoustic models used to predict the acoustic output parameter achieved in the imaging field under similar conditions.

In another preferred embodiment, an acoustic output parameter of a transmitted ultrasonic beam in a region in an ultrasound image is determined. Then, an indication of the determined acoustic output parameter is provided along with an indication of where in the ultrasound image the region is located. For example, in addition to determining and displaying the mechanical index, the ultrasound system can also display a visual indicator (e.g., a dot) on the displayed ultrasound image to indicate a location in the image that is associated with the displayed mechanical index. As another example, instead of or in addition to displaying a visual indicator on the image, the range associated with the mechanical index can be displayed. With this preferred embodiment, a user will know the spatial location of the mechanical index (or other acoustic output parameter) in the ultrasound image. If the mechanical index occurs at a location of interest to the user (such as a location of contrast agent), no further action may be required by the user.

However, if the location of the mechanical index is not at a location of interest to the user, the above-described preferred embodiments can be used to determine an acoustic output parameter in another location.

It is important to note that any of the various aspects of any of the preferred embodiments can be used alone or in combination. For example, although not shown in the flow chart 200 of FIG. 2, acts 230, 235, 240, and 245 can be performed together, separately, or not at all. As another example, the ultrasound system can automatically adjust operating parameters to achieve a specified acoustic output parameter in an automatically-selected region (instead of or in addition to a user-selected region) by automatically adjusting an operating parameter of the system.

Further, in another alternate embodiment, a region is selected in an ultrasound image that does not correspond to the location of a peak acoustic output parameter (e.g., the mechanical index). The region can be automatically selected by the ultrasound system (such as when the region is automatically selected at a specified image depth or at the transmit focus of the transmitted ultrasonic beam) or can be selected by a user. The ultrasound system then determines and provides an indication of an acoustic output parameter for the region. As mentioned above, any of the various aspects of these preferred embodiments can be used with this alternate embodiment.

It is intended that the foregoing detailed description be understood as an illustration of selected forms that the invention can take and not as a definition of the invention. It is only the following claims, including all equivalents, that are intended to define the scope of this invention.

The following is a preferred method of determining various acoustic and thermal parameters of a transmitted ultrasonic beam.

/ 2

```
PMS Model Parameter Determination:
====================================

(formerly: "pms.calc" Calculated Power Mgmt Parameters)
(Stefan Schmitz: 94/01/28)
(update:    96/01/02)
(update:    96/10/02 new C-factor vs Vpp algo)
(update:    97/10/15 acoust. conversion weight by bandwidth)
(moved:     98/04/07 to /people/pmsw/dev/spcalc; put under SCCS
            was in interleaf; made softlink there:
                System5->Acuson->adia->Scanning-specs->
                Other-Features->pms_calc)
```

This document describes the parameters that are the outcome of
first Power Measure ("spmeas") and then Power Calc ("spcalc").
They will be entered into the Imaging Spec. They allow the
machine to calculate online the values for the various acoustic and
thermal parameters of the ODS model.

(Note: parameters for temperature rise at surface, delta-T, are not included)

There are nine model parameters each depending on up to 5 independent
parameters. The two tables below summarize:
 1. the independent parameters (actually a superset of them)
 2. the nine model parameters

```
Standard single line meas params:
==================================
all = (frq, ang, tx, loc, apo, fnu, cyc, vol)

frq = output carrier frequency
ang = line angle
txt = azimuthal transmit focus
loc = measurement location (range)
apo = apodization type
fnu = f-number
cyc = pulse length in cycles (q-number)
vol = transmit peak-to-peak voltage
```

Table of calculated Pwr Mgt Param that go into the IS
and their dependencies
=====================================================

| IS param: | frq | ang | txt | loc | apo | fnu | cyc | vol | comment |
|---|---|---|---|---|---|---|---|---|---|
| 1) a_avg[1] | yes | | | | | yes | | | acoustic conversions |
| 2) a_max[1] | yes | | | | | yes | | | acoustic conversions |
| 3) z_el[mm] | yes | yes | | | | | | | elevational beam model |
| 4) L0y[mm] | yes | yes | | | | | | | elevational beam model |
| 5) e_el[1] | yes | yes | | | | | | | elevational beam model |
| 6) b[1] | yes | yes | | yes | | | | | azimuthal beam model |
| 7) e_az[1] | yes | yes | | yes | | | | | azimuthal beam model |
| 8) C_ii[1] | yes | yes | yes | yes | | | | yes | C-factors |
| 9) C_mi[1] | yes | yes | yes | yes | | | | yes | C-factors |

/3

```
1+2) acoustic conversion:   avg(freq, cyc) and a_max(  q,cyc):
================================================================== a_avg (freq,cyc)[1] = average (over: ang, tx, loc, apod, f#, volt)
                      of meas (over: ang, freq, tx, loc, apod, f#, cyc)
                        of
                          E_pa_ac[W]        W_pa_ac[W]
                          ----------  or    ----------  (either is selectable)
                          E_pa_el[W]        W_pa_el[W]
             .      = pulse average acoustic conversion a_max (freq,cyc)[1] = average (over: ang, tx, loc, apod, f#, volt)
                      of meas (over: ang, freq, tx, loc, apod, f#, cyc)
                        of
                          W_min_ac[W]
                          -----------
                          W_min_el[W]
                    = pulse max acoustic conversion E_pa_ac[uJ] = measured pulse_energy[uJ]
            = 0.01 * PII[uJ/cm^2] * x_eebw[mm] * y_eebw[mm]
x_eebw, y_eebw are the energy equivalent beam widths W_pa_ax[W]  = E_pa_ac[uJ] / meas-tau[usec]

meas-tau    = measured pulse length (risetime algorithm)

E_pa_el[W]  = W_pa_el[W] * elec-tau[usec]

W_pa_el[W]  = electrical pulse average power calculated by Sequoia elec-tau    = S calculated pulse length (risetime algorithm)

W_min_ac[W] = measured pulse-max Pr power

Pr * Pr
W_min_ac    = -------  * x_eebw * y_eebw
              rho * c
max Pr rarefaction pressure in MPa
rho density of water = 1g/cm3
c    speed of sound in water = 1.5246 mm/usec W_min_ac is calculated by meas; so it's in the input for calc Note that the measure quantities are not tissue attenuated.  If the actual
measurements were attenuated, the corresponding un-attenuated values must
be calculated first.

need from Acq:
==============
W_pa_el[W]: electrical pulse average power
tau_el:    electrical pulse duration:
E_pa_el = W_pa_el * tau_el
W_min_el[W]: electrical min peak power (neg excursion peak)

processing:
===========
-> At first the both acoustic conversions are calculated for each distinct
   modulation frequency and cycle count.  There are separate values for
```

14 pulse average and pulse max.

-> A desired output sample grid is picked:
  1. for the output carrier frequency the grid is equal to the distinct modulation frequencies (usm_mod_freq)
  2. for the cycle count the grid is equal to the distinct cycle counts (usm_cyc)

-> Foreach grid point (distinct pair of sample grid freq and cycles):

Compute weighted sum average of all (not-rejected) measurements, so that $$a\_avg/max(gridFreq_i, gridCycle_j) = \frac{\sum_{measurements} a\_avg/max * weight}{\sum_{measurements} weight}$$

where weight = exp ( - ac_weight_exp_fact * distancce^2 )

where distance is given by one of two choices:

if spcalc option ac_weight_by_bandwidth is non-zero $$distance^2 = ac\_weight\_exp\_fact\_freq * \left(\frac{gridFreq_i - measFreq}{avg\text{-}measFreq}\right)^2$$

$$+ ac\_weight\_exp\_fact\_cycl * \left(\frac{1}{gridCycle_j} - \frac{1}{measCycle}\right)^2$$

else (when ac_weight_by_bandwidth is zero; older approach)

$$distance^2 = ac\_weight\_exp\_fact\_freq * \left(\frac{gridFreq_i - measFreq}{1\ MHz}\right)^2$$

$$+ ac\_weight\_exp\_fact\_cycl * \left(\frac{gridCycle_j - measCycle}{1\ cycle}\right)^2$$

where ac_weight_by_bandwidth, ac_weight_exp_fact, ac_weight_exp_fact_freq and ac_weight_exp_fact_cycl are spcalc input options (numbers). avg-measFreq is the average of the (not-rejected) measFreqs.

Note: The weighted sum avoids problems of grid resampling, especially "grid holes" at the edges which caused bad results due to constant extrapolation and fixed order over dimensions in which these holes were filled.

The newer weighting approach (by bandwidth when option

/5

```
       ac_weight_by_band    th is non-zero) moves lon   ulse length much
       closer as was indicated by measurements.  This was introduced in August
       1997.

Options (see comments in template file: spcalc.options):
============================================================
-> We reject measurements whose ratio of meas-tau/elec-tau is outside
   a desired range.  The low and high ends of this range are input
   options. (defaults 0 and 999, i.e. turned off)

-> the a_avg can be computed using pulse average power or pulse energy
   where  energy = pulse-average-power * pulse-length.  Which one is
   used is user selectable.

-> a_avg and a_max can be computed as the average between them, in that
   case they are the same (and equal to the average). For backwards
   compatibility.

-> a_avg and a_max can be computed to be a function of frequency only
   with the same value for the different cycles.  For backwards
   compatibility.

-> ac_weight_by_bandwidth, ac_weight_exp_fact, ac_weight_exp_fact_freq
   and ac_weight_exp_fact_cycl (see above)

-------------------------------------------------------------------------

2) elev focus:
============== z_el (freq, angle)[mm] = meas (over: freq, angle)
                         of min elev beamwidth location processing:
===========
-> we accept only those measurements whose elev focus location is
   within a margin of the legal range limits -> we set the output grid frequencies and anles equal to the distinct
   modulation frequencies and distinct usline angle.

-> we bin the data for (distinct and sorted ) output carrier frequencies
   and angles.  Note that the frequency bins do not (necessarily) coincide
   with the output grid frequencies.

-> we compute the average for each bin

-> for each output grid angle, we resample the frequencies to the output grid
   frequencies by interpolation and constant extrapolation (this fills
   in holes in freq as well)

-> we fill in any remaining holes in angle (by interpolation or constant
   extrapolation)

-------------------------------------------------------------------------

3+4) elev beam width at focus (L0y) and effective aperture factor (e-factor):
==============================================================================

L0y (freq, angle)[mm] = average over (tx, loc)
```

*16*

```
                            calculated elev beamwidth    focus
                            from meas (over: freq, angle, tx, loc)

e-factor(freq, angle)[1] = average over (tx, loc)
                            of calculated elev effective apeture factor
                            from meas (over: freq, angle, tx, loc)

z1       = range of meas loc
     zfy      = elev focus
     Ly       = ee beamwidth at range (measured)
     LSy      = ee beamwidth at surface (calc'd) = a0y * e-factor
     L0y      = ee beamwidth at focus (calc'd)
     a0y      = elev aperture
     e-factor = elev beamwidth at surface factor = LSy / a0y /      z1[mm]  \
     let  u      =     ( 1 -  -------   )
                        \     Zfy[mm]  /

+-------------------------------------
                            |      / /LSy[mm]\ 2    \     2
     Ly(z1) [mm]  = L0y[mm]*\|1 + ( ( ------- )  - 1 ) * u
                            \|     \ \L0y[mm]/      /

+-------------------------------------
                            |         2              2       2      2
                 =         \| L0y[mm]    + ( LSy[mm]   - L0y[mm]  ) * u
                            \| solved for L0y:
                            +-----------------------------------
                            | Ly(z1)[mm]^2 - LSy[mm]^2 * u^2
     L0y[mm]     =         \| -------------------------------
                            \|          1 - u^2 relative average-sum-weight for L0y:

/ L0y * (1-u^2) \^2
                 w  =  ( --------------- )
                        \    Ly(z)^2    / solved for e-factor = LSy / a0y:
                                  +-----------------------------------------
                        1        | Ly(z1)[mm]^2 - L0y[mm]^2
     e-factor   =      --- *    \| ------------------------- + L0y[mm]^2
                       a0y       \|          u^2 relative average-sum-weight for e-factor:

/ e-factor * a0y^2 * u^2 \^2
                 w  =  ( ----------------------- )
                        \       Ly(z)^2          /

Notes:
======

When calculating L0y:
======================
     As for elev focus we ignore measurements whose measurement
```

*17*

```
range is too clos   o the softlimits.

Only if Ly > abs( (z-zfy) / zfy) * LSy   (when  z < 2 * zfy)
is the number under the root positive.  If not, the beamwidth
is too narrow and cannot be fit to our formula.  We will simply
ignore these cases.  That should not happen, if we measure
really close to the focus.

In cases where L0y comes out to be larger than the LSy using
the formula above we will ignore the measurement.  However,
In the model calculation, we will then use a linear formula
for these cases (where the beamwidth at focus is larger than
at the surface).  The formula is:
                                                    zfy[mm]
   L0y[mm] = LSy[mm] + ( Ly(z1)[mm] - LSy[mm] ) * -------
                                                    z1[mm]

When averaging over tx and meas loc, we'll perform a
weighted sum average, where the relative weights are
proportional to the inverse square of the estimated error.

d-L0y
error in L0y =  -------- * const * Ly(z)
                 d-Ly(z)

Ly(z)^2
             = const * ----------------
                        L0y * (1 - u^2)

relative weight:

/ L0y * (1-u^2) \^2
         w = ( --------------- )
              \    Ly(z)^2    /

Note: the weight becomes zero for z1=0 or z1 = 2 * zfy
          because the function must pass through Ly(0 or 2*zfy) = LSy
          nor matter what was measured.

When calculating e-factor:
===========================
    As for elev focus we ignore measurements whose measurement
    range is too close to the softlimits.

When calculating e-factor it may become complex or infinite
    (if u^2 = 0 or Ly(z1)^2 < (1-u^2)*L0y^2).  In that case the
    measurement is ignored.

When averaging over tx and meas loc, we'll perform a
    weighted sum average, where the relative weights are
    proportional to the inverse square of the estimated error.

d-e-factor
    error in e-factor = ---------- * const * Ly(z)
                          d-Ly(z)
                                        Ly(z)^2
                        = const * ----------------------
                                   e-factor * a0y^2 * u^2
```

*18* relative weight fc -factor:

$$w = \left( \frac{e\text{-factor} * a0y^2 * u^2}{Ly(z)^2} \right)^2$$

processing:
==========
1. Using a starting values for e-factor, we calculate the L0y.
   The processing is as for elev focus, except we use a weighted
   sum average (instead of straight averate) with the above formulas
   for e-factor and summing weights.
2. Then using the resulting L0y sampled to the final output grid, we
   calculate e-factor. The processing is as for 1.
3. Then iterate over 1 and 2. Where the iteration count is an input
   option.

Options (see comments in template file: spcalc.options):
========================================================
-> starting e-factor (defaults to 0.666667)
-> number of iterations (defaults to 1)
   (each step counts as one iteration, so if n=1 we only fit L0y, if
   n=2 we fit L0y and e-factor once, if n=3 we fit b-factor twice but
   the e-factor only once, etc.)

---------------------------------------------------------------------

6+7) azim beamwidth at focus and effective aperture factor (b- & e-factor):
=========================================================================== b (freq,angle,apod) [1] = average(over: tx, loc, f-num)
                          of meas(over: angle, freq, tx, loc, apod, f#)
                          of:
                              b-factor and e-factor This is very analogous to the elev processing! So the above formulas
apply except "y" is replaced by "x", and the focus, zfx, is no longer
measured but just taken to be the nominal xmt focus. There is also
the additional dependency in the apod type, which only affects
the binning, resampling, output grid and logistics like that.

The only "real" difference is that the model parameter is not the
"beam width at focus" (L0x), as it is for elev., but the b-factor, where:

L0x = b-factor * lambda * f# lambda  = wavelength = freq / speed
          speed   = 1.5246 mm/usec; speed of sound in water
          f#      = focus / aperture
          a0x     = aperture
          zfx     = focus L0x[mm] * LSx[mm] * freq[MHz]
       so: b = -----------------------------
                  speed[mm/usec] * zfx[mm]

Note: we use the true f# in the above formula not the effective one as in
a previous version of spcalc!

The averaging-summing-weight for the b-factor is slightly different

*19* then for L0y, but just by    caling factor. Here's the story":

>  For measurements away from the focus (especially when
>  at a depth near twice the focus) small variations in
>  the measurement can cause very large variations in the
>  b-factor value.
>
>  Therefore we weight each term in a sum by the inverse square
>  of the expected measurement error on b.
>
>  Expected measurement error on b is:
>
>     const * derivative of b-factor w.r.t Lx(z) * error in Lx(z)
>
>  and the error in Lx(z) is assumed to be proportional to Lx(z)

```
d-b         Lx      1                         z1
---- = b * ---- * -------      with u = 1 -  ---
d-Lx       L0^2   1 - u^2                    zfx Lx^2     1
     expected error = const * b * ---- * -------
                              L0^2   1 - u^2
```

>  relative weight:
>
> ```
>        / L0^2    (1-u^2) \^2
>   w = ( ---- *  -------  )
>        \ Lx^2      b    /
> ```
>
>  Note: the weight becomes zero for z1=0 or z1 = 2 * zfx
>        because the function must pass through Lx(0 or 2*zfx) = LSx
>        nor matter what was measured.

processing:
==========

-> for each combination of (sorted) distinct values for output carrier
   freq, angle and apod type we calculate the weighted sum average of the
   b-factor using the initial (or latest) e-factor.

Note: Only if Lx(z) >= u * LSx does b-factor to have a real solution.
   Otherwise we ignore the meas condition.

-> we resample the results to the final output grid (first in freq, then
   in angle, but not in apod type)

Note: we do NOT resample over the apod type dimension. However, there
   cannot be any more any isolated holes, because we resampled (filled
   in for the other two dimensions.) The only holes could be a complete
   "plane", meaning for a fixed apod type, there are no good values for
   any frequency or angle.  I would certainly be wrong to fill in this
   case (which would be rather pathological indeed)

-> Now repeat the above steps for the e-factor (formula for it and for
   its summing weight are as for elevation with L0x = b-factor * lambda *
   f-number. Use the b-factor (resampled to final output grid and then
   interpolated back to desired values) as calculated previously.

-> Iterate over b-factor (given new e-factor) and then e-factor (given new b-factor)

Options (see comments in template file: spcalc.options):
========================================================
These are the same as for elevation:
-> starting e-factor (defaults to 0.666667)
-> number of iterations (defaults to 1)

-----------------------------------------------------------------------------

8) C_ii: Isppa/Ispta/PII c-factor:
====================================

C_ii (freq, ang, tx, apod, volt)[1] = maximum (over: loc, f#, cyc, sppa/spta)
                                     of meas (over: all)
                                        of C_ii The C_ii comes in three choices: C_isppa, C_ispta, and C_pii.  Only one
is in the output (nominally called C_isppa).  By spcalc input option, we
can choose either of the three, any pairwise max or the overall max of the
three for each measurement.  The standard and default is:

C_isppa_final = max (C_ispta, C_pii)

C_isppa, C_ispta, C_pii:

Isppa_meas[W/cm2]
         C_isppa = -------------------
                    Isppa_calc[W/cm2]

and

Ispta_meas[W/cm2]
         C_ispta = -------------------     for RES->oo
                    Ispta_calc[W/cm2]

where RES->oo means in the limit where
                                     the res/pan box is much larger than the beam width.

and
                    PII_meas[uJ/cm2]
         C_pii = -------------------
                    PII_calc[uJ/cm2]

where:
------
                            /         W_ac_pa[W] * 10^(-0.003*freq[MHz]*z[mm]) \
Isppa_calc[W/cm2] = max    ( 100 *  ------------------------------------------- )
                    over z \              A_ee_beam(z) [mm2]                   /

PII_calc[uJ/cm2] = Isppa_calc[W/cm2] * el_tau[usec]

In practice "max over z" means evaluating at z=0 z=z_elev_focus and z=z_focus
and picking the maximum of these.

Note:   W_ac_pa[W]      = a(freq)[1] * W_el_pa[W]
        A_ee_beam[mm2]  = Lx(z)[mm] * Ly(z)[mm]

```
Cispta:
-------
The limit of RES->oo is used because the res box size is not known, nor
would it be desirable to calculate the above for all res-box, line spacing
combinations.  And since the limit RES->zero is handled by the PII or Isppa
case we go for the large RES box limit:

PII(z) * Lx_meas(z) * NF
Ispta_meas (for RES->oo) = ------------------------ * 10^(-0.003*f_meas*z) .
                                   FT * RES Note: Lx * NF / RES is the BOF (or BOF * FSC)

a * E_pa_el * NF
Ispta_calc (for RES->oo) = -------------------- * 10^(-0.003*f_mod*z)
                           RES * Ly_mod(z) * FT where: Lx,y beamwidth in azim or elev (either measured or modelled)
       NF: number of firings in scan
       FT: frame time
       a:  model's acoustic conversion
       E_pa_el[W] = electrical pulse energy calculated by Sequoia
                  = pulse power times tau The C_ispta can optionally calculated two ways:

1) The ratio is evaluated for all measurement z's and the max is taken:

PII(z) * Lx_meas(z) * Ly_mod(z)     10^(-0.003 * f_meas * z)
       Cispta = ------------------------------- *  --------------------------
                         a * E_pa_el                10^(-0.003 * f_mod  * z)

The value for z is the meas range in all quantities, meas or model.
      In short:
                                            meas-term(z)
          C_ispta = max over measured z of  ------------
                                            calc-term(z)

2) z is treated like it is for C_isppa and C_pii.  The meas-term is
      "maxed" over the meas ranges and the calc term is "maxed" over
      z=0 and foci.
      In short
                    max over measured z of meas-term(z-meas)
          C_ispta = ----------------------------------------
                    max over z=0 and foci of calc-term(z-calc)

This second way is analogous to C_isppa and C_pii

* THIS SECTION WAS REPLACED:
*
* then fitC(V) as fct of Vpp^2 and get:
*
*        C_0 (freq, ang, tx, apod) [1]
*        V_0 (freq, ang, tx, apod) [V]
*        P+  (freq, ang, tx, apod) [1]
*        P-  (freq, ang, tx, apod) [1]
*
```

```
* where:
*
*              /       /  V    \2 \
*     C(V) = C_0 ( 1 - P+ ( --- - 1 )  )     for V > V_0
*              \       \ V_0   /  /
*
*              /       /  V    \2 \
*     C(V) = C_0 ( 1 - P- ( --- - 1 )  )     for V < V_0
*              \       \ V_0   /  /
*
* finding C_0 and V_0:
*
*     C_0 = max over V [ C(V) ]
*     V_0 = V that maximizes C(V)   or C(V_0) = C_0
*
* finding P+/-
*                         / V_0^2     C_0 - C    \
*     P+ = min over V > V_0 ( -----  *  ------------ )
*                         \  C_0      [V - V_0]^2 /
*
*                         / V_0^2     C_0 - C    \
*     P- = min over V < V_0 ( -----  *  ------------ )
*                         \  C_0      [V - V_0]^2 /
*
*     P+/- will be set to zero if there are no C(V) with
*     V>V_0 or V<V_0 respectively
*
* END OF REPLACED SECTION
*
**** MORE DELETED STUFF
* (C-factor fitting for voltage grid:
*======================================
*For each fixed set of freq, ang, tx we will calculate a set of
*Cn for fixed voltage grid values Vn n=1..N, such that
*
*  1) C*V^2 is piecewise linear in V^2, where the pieces are bounded
*     by these Vn
*
*  2) All measured points, C*V^2, lie on or below the piecewise linear
*     curve (and NEVER above it)
*
*  3) C*V^2 is assumed to go throug the origin, i.e. is zero for V=0

*The algorithm:
*---------------
*1) start in first V interval: 0<V<V1 and find min slope that curve can
*    have so that no measured point lies above it.
*    This results in the value C1*V1^2 at the first grid point V1.
*    One can extend the interval that is used to include portions of
*    the NEXT interval with an optional grid-overlap factor.  So that
*    all measurement points that lie in a larger interval are considered.
*    The result is then still calculated for the current grid's endpoint
*    and the procedure repeats.  So, without grid overlap, we use

*    for i-th interval:    V_(i-1)^2   <   V   <  V_i^2

*    with a grid overlap factor (GOF):

*                          V_(i-1)^2   <   V   <  V_i^2 + GOF * [V_(i+1)^2 - *V_i^2
```

∂3

```
*    Again the resulting ma   lope for the current inte   il is still
*    used to calculate C*V^2 at V_i only (with or without grid-overlap-factor)

*2)  repeat the step for the next higher voltage interval, until all
*    grid voltages intervals are done.
*
*********** END OF DELETED STUFF
```

C-factor voltage grid computation and fitting to grid: .
===========================================================
This was algorithm was changed Sept 26, 1996 (see the old version above).

1. For each unique set of freq, angle, tx-focus and apod type, we compute
   all "raw" C-factors as function of Vpp and call this set a "case".
   We then compute y as a function of x, where y is C-factor x Vpp^2 and
   x is Vpp.  The final fit will be a piecewise linear curve of y vs x 2. For each case we compute its convex hull, which consists of a subset
   of the raw x-y pairs and the point (0,0).  The hull is computed by
   first adding point (0,0) to it.  We then find that raw x-y pair with
   the largest slope and add it to the hull.  We then find that raw x-y
   pair with x > x0 and y > y0 (where x0-y0 is the last added hull point
   which is also the one with the largest x and y values) which has the
   largest slope computed from x0-y0, i.e.

$$\max \text{slope}(x_i, y_i) = \frac{y_i - y_0}{x_i - x_0} \text{ for all } x_i > x_0 \text{ and } y_i > y_0$$

In other words, the next hull point is (xi,yi) where xi > x0 and yi >
y0
   and slope(xi,yi) is max of all points with xj > x0 and yj > yo.

We repeatedly add hull points until no more raw points with xi > x0
   and yi > y0 can be found.

3. We set the initial x-grid values to just two values: 0 and the max x for
   all hull cases.

4. We fit each hull case to the grid as follows.  Add the point (0,0) to
the
      fit.  Then for each x-grid value compute the maximum slope w.r.t the
      previous x-grid value and compute the intersection of a line
      with that slope from the previous grid point (x,y) and the current grid
      line (vertical line through the x-grid).  That is the new grid point.
      Then repeat until all grid points are covered.
   In other words y-next-grid = y-last-grid + max-slope * (x-next-grid - x-last-grid)

$$\text{where max-slope} = \max \text{ of } \frac{y_i - \text{y-last-grid}}{x_i - \text{x-last-grid}} \text{ over all}$$
         xi > x-last-grid and yi > y-last-grid.

If the max slope is zero or negative or if there are no hull points with
   x > x-last-grid-point, then extrapolate from the last hull point as
   follows:

$$y(x\text{-grid}) = \frac{y\text{-max-hull}}{x\text{-max-hull}} * x\text{-grid}$$

Note: the hull point with the largest x also has the largest y.

5. Compute the error between the hull and the fit at each null point and at each grid point for all cases. Extrapolation is as explained above ("constant C-factor extrapolation"). If the max absolute error is larger than an input tolerance add another grid point. The grid point is chosen by finding the point with the largest error (either a point on the hull or on the grid for one case). Find the next lower hull point for that case (unless that's already in the grid, then pick the next lower) and add that point to the grid.

6. Repeat steps 4 and 5 until the max absolute error is less or equal to the tolerance.

7. Now we repeatedly try to remove grid points again. We remove each grid point in turn and compute the max absolute error for all cases. If this error stays less or equal to the tolerance the point is removed. We pass over the grid from low to high x values and then in reverse until no further reduction can be achieved 8. The fitted C-factors are the ratios y/x of the fitted curves for all case. The Vpp grid consists of the square roots of the x-grid values.

Note: in the above "all cases" means for both Ispta and MI (and all freq, angles, foci and apod types)

processing:
==========
- foreach distinct value of modulation frequency, angle, azim xmt focus, and apod type: calculate the measured and model parameter (tissue attenuated) and form the ratio. That is the C-factor as fct of volt. Record the C-factor, the voltage (Vpp), and the measurement's output carrier frequency. Here we apply the tau-rejection criterion: measurements whose ratio of meas-tau/elec-tau lies outside an option input range are ignored. (as for acoustic conversion)

- compute the grid and the fitted C-factors as described above for each case.

- For each of the THREE indept parameters (angle, focus, apod type):
  Sort the Cn values by (averaged) output carrier frequency
  and resample that list to the (distinct; sorted) modulation frequencies.

- This gives a regular rectangular four dimensional table with. Fill in holes by resampling over foci and angles (but NOT apod types; see Note under processing for azim beamwidth factor above)

Options (see comments in template file: spcalc.options):
========================================================
- low and high tau rejection ratios (see acoustic conversions)
- max absolute error for grid calculation and fitting in percent
- range treatment for C_ispta (see above: either calculate ratio at the measurement ranges and take max OR take max of meas-term over meas. ranges and the max of calc-term over z=0 & foci and then form the ratio)
- by default, we create the files spc_vsub.dat and spc_vcfa.dat instead
  of the spc_val.dat file.

---

9) c_mi: MI c-factor:
=====================

```
c_mi (freq, ang, tx, apod)[1] = maximum (over: loc, f#, cyc)
                                of meas (over: all)
                                of
                                    /MI_meas\ 2
                                   ( ------- )
                                    \MI_calc/
```

$$MI\_meas[1] = \frac{Pr(z)[MPa]/MPa * sqrt(10^{(-0.003*freq[MHz]*z[mm])})}{sqrt(freq[MHz]/MHz)}$$

$$MI\_calc = \max_{over\ z} \sqrt{\frac{W\_min\_a[W] * rho[g/cm3] * c[mm/usec] * 10^{(-0.003*freq*z)}}{A\_ee\_beam(z)[mm2] * freq[MHz]}}$$

In practice "max over z" means evaluating at z=0 z=z_elev_focus and z=z_focus
and picking the maximum of these.

```
Note:   Pr^2      = (W_min_ac / A_ee_beam) * rho * c
        rho       = 1 g / cm^3 water density
        c         = 1.5246 mm / usec speed of sound in water
        W_mim_ac  = a(freq) * W_min_el
        A_ee_beam = Lx(z) * Ly(z)
```

The calculation of the Cn values for the voltage grid values Vn (n=1..N)
is the as for C_isppa.

processing:
==========
same as for C_isppa

Options (see comments in template file: spcalc.options):
========================================================
Three of the options that apply to C_isppa also apply to C_mi:
- low and high tau rejection ratios (see acoustic conversions)
- set of output grid voltages
- voltage grid overlap factor (see C_isppa)
- by default, we create the files spc_vsub.dat and spc_vcfa.dat instead
  of the spc_val.dat file.

---

Electrical conductance rescaling:
=================================
The usm machine calculates the electrical power terms
(pulse average and pulse min or max power) by multiplying three
terms: a voltage term, a apod sum term and the electrical conductance.
This elec. conductance is a table provided by Power Management to the machine. The table c  ists of pairs of elec. co.  ctance (in uMho) vs
output carrier frequency.  During online operation it is interpolated
to produce an electric conductance value for the current output carrier
frequency.

spcalc provides for the capability to change the electrical conductance
after the measurements are complete. It takes a new table of electrical
conductance vs output carrier frequencies and rescales the electrical
power terms according to this new conductance. This of course will
change the model parameters, namely the acoustic conversions and the
C-factors.

It is important that the same electrical conductance table is loaded
into the machine, that was used as input to spcalc.

Here are the formulas:
=======================
```
old_conductance[uMho]      read from machine during measurment
old_W_pa_el[W]             read from machine during measurment
old_W_min_el[W]            read from machine during measurment
new_conductance[uMho]      new value: interpolated from separate input
                           table to spcalc.
```

In all equations above that use the electric poer values
(acoustic conversion, C-factors), we do this:

```
W_pa_el   = old_W_pa_el  * new_conductance / old_conductance
W_min_el  = old_W_min_el * new_conductance / old_conductance
```

Summary of Parameters calculated by Acq needed during Power Meas:
=================================================================
the single line xmt parameters, plus

```
aox[mm]:         xmt azim aperture
W_pa_el[W]       electrical pulse average energy
W_min_el[W]      electrical min peak energy (neg excursion peak)
V[V]             xmt voltage
conductance[umho]:
elec-tau[usec]   :
```

Output of Power Calc (spcalc):
==============================
The output is produced twice: once formatted for Z and once for S
The program also produces a text file that explains the output formats.
There are also debug output files that can be turned on. They are
also described in the "explanation file".

Output for Z:
=============
NOTE:  This is currently still the backwardsly compatible format for
       an earlier version of the model. Certain options (in spcalc.options)
       must be set correctly (see the option inputs file). Also the
       azim b-factor is divided by 1.5 for backwards compatibility.

The output is in mgl format and goes to a single file, with a table
for each PMS parameter. Each table records the parameter value and
the grid sample values for the independent paramteres:

1) acoustic conversions: 2D-table

∂7

```
        ac-conv        a(freq)

2) elev focus and min beam width: 3D-table z_el      L0y(freq, angle)      freq      angle 3) azim beam width parameter, b: 3D-table b(freq, angle)/1.5       freq       angle        .

4) Isppa C-factor

C       freq       angle      tx       apod       volt

5) MI C-factor

C       freq       angle      tx       apod       volt
```

Output for S:
=============
1) S will do online interpolation in all six dimensions and, therefore,
   the imaging spec will store exactly what pms-calc produces. That is
   no interpolation or resampling when the imaging spec is created.

2) By default, we generate three data files to fill three tables.
   The files (tables) are: spc_grid.dat (pms_meas_grid) spc_vsub.dat
   (pms_meas_sub_values) and spc_vcfa.dat (pms_meas_c_factor). For
   backwards compatability, we can generate the two data files
   spc_grid.dat and spc_val.dat to fill the pms_meas_grid table and
   the obsolete pms_meas_values table. pms_meas_grid contains the 6
   independent variables (freq, angle, focus, apod type, cycles, volt),
   and the other table(s) contain the nine dependent ones.

3) The pms_meas_sub_values table depends on the independent variables:
   freq, angle, apod type, and cycle count. The pms_meas_c_factor
   depends on: freq, angle, focus, apod type, and voltage. Splitting
   the data into two tables allows for a great savings in storage
   for the IS database.

The pms_meas_values table munges all the data into a single
   table. This is still supported through the spcalc option
   "make_spc_val = 1". By default, data for the two new tables,
   pms_meas_sub_values and pms_meas_c_factor, is made instead.

4) The two tables pms_meas_sub_values and pms_meas_c_factor are
   represented in acuisition software by the structures:

```
        struct PmsMeasSubValuesIsm
        {
            Float    acoustPulseAvgConv;
            Float    acoustPulseMaxConv;
            Float    elevFocusMm;
            Float    elevMinBwidthMm;
            Float    elevEffAperFactor;
            Float    azimBFactor;
            Float    azimEffAperFactor;
        };
``` and

```
    struct PmsMeasCFactorIsm        //PMS data C factor values
    {
        Float   isppaCFactor;
        Float   miCFactor;
    };
```

(both from the AcqIsmDataStruct.h file)

The table of the "9" will have a column for each parameter and its six dimensional matrix is stored in linear fashion as column vector. In practice, that means an array of a struct like this:

```
    struct PmsMeasValuesIsm         //PMS data values
    {
        Float   acoustPulseAvgConv;
        Float   acoustPulseMaxConv;
        Float   elevFocusMm;
        Float   elevMinBwidthMm;
        Float   elevEffAperFactor;
        Float   azimBFactor;
        Float   azimEffAperFactor;
        Float   isppaCFactor;
        Float   miCFactor;
    };
```

So, for instance, if we had measured "everything" for 3 frequencies, 2 angles, 5 foci, 4 apod., 6 cycles and 7 voltages the table would have 3 x 2 x 5 x 4 x 6 x 7 = 5040 rows 5) The sample grid values for each of 6 independent parameters are also packed into a single table. It has six columns one for each parameter. The number of rows is the max number of values for any of the four paramters. Therefore, we will pad the column vector with a terminator value for those parameters whose value lists are shorter than the number of rows.

```
    struct PmsMeasGridIsm           //PMS grid definition
    {
        Float   outputCarrierFreqMHz;
        Float   usLineAngleDeg;
        Float   xmtFocusDepthMm;
        Int     baseApodId;
        Float   cycleCount;
        Float   xmtVppV;
    };
```

So, in the above example (3 freq, 2 angles, 5 foci, 4 apod, 6 cycles, 7 volt), this table would have 7 rows. For freq, angles, apod and cycle the last 4,5,2,3, and 1 rows would have a terminator value (perhaps -1000000).

Notes:
======
1) spmeas will attempt to measure an angle.
   If the elev focus cannot be found (because it is too shallow) the program will "say" so but go on.

```
         If the peak for a parti   ar xmt focus cannot be fc   . the program
         will go on to the next xmt focus.  For very large angle, perhaps no
         xmt focus might have data.  These holes will be "filled" in by
         resampling to the output grid. (see above)

Summary description of handling the jitter of the output carrier freq:
======================================================================
This is just a recap of what is written above in the various "processing"
sections:

1) find list of distinct modulation freq the values will also serve as
   the output (sample) grid output-carrier-frequencies 2) find lists of distinct angles, xmt foci, apod types and cyles 3) foreach distinct output grid value pair of oc frequency and
   cyles:

calculate the weighted sum averages for all acoustic conversions.
   Measurements that are "closer" to the output grid point have a higher
   weight than meas that are "farther".  Still, all measurements are
   averaged for a single grid point.

4) foreach distinct output carrier freq and distinct angle calculate and average "z_el" and "L0y" and e-factor and f_oc interpolate these three back to the list of output grid freq values 5) foreach distinct output carrier freq and distinct angle and apod type calculate and average azim b-factor and e-factor and f_oc interpolate these three back to the list of output grid freq values 6) foreach distinct modulation freq, angle, xmt focus, apod type calculate C(V) and average f_oc 7) from C(V) determine Cn(Vn)

8) interpolate them back to output list of output carrier frequencies.
```

30

```
                Online PMS Model Calculation:
                =============================
                (formerly: "pms.online" Online Calculation of acoustic
                                        and thermal parameters)
                (Stefan Schmitz: 94/01/31)
                (update    97/05/06)
                (update    97/10/16; Ispta change for z=0 for rel 2.5)
                (moved:    98/04/07 to /people/pmsw/dev/spcalc; put under SCCS
                           was in interleaf; made softlink there:
                              System5->Acuson->adia->Scanning-specs->
                              Other-Features->pms_calc)
```

This document describes the calculation of the acoustic and thermal
parameters by Sequoia when it is in operation. The parameters
are for FDA and internal regulations. Some parameters will be
regulated, others merely displayed.

There are two groups: short time constant paramters (STC) that apply
for a single firing and long time constant parameters (LTC) that
are averaged over long times (full frame).

STC:
   1) Isppa_t
   2) MI

LTC:
   4) Ispta_t
   5) TIS, TIB, TIC
   6) dT_skin, dT_air

Parameters for IEC1157

Headrooms

Note: dimensions are in [], e.q. [mW/cm^2]
  [1] means dimensionless
  square of units appends "2" or "^2", i.e.: [V2] or [V^2]
-----------------------------------------------------------------------

1) Isppa_t [W/cm^2]
   ================

```
                                     /              W.3_pa_acoust[W]  \
Isppa_t[W/cm^2] = 100 * maximum ( c_sppa[1] * ----------------------- )
                         over z   \              A_ee_beam[mm^2]     /
```

A_ee_beam(z,freq,ang,zfx,a0x,apod) [mm^2] = Lx[mm] * Ly[mm]

Lx(z,freq,ang,zfx,a0x,apod) [mm] =

```
              +----------------------------------------------
              |      / /LSx[mm]\ 2    \    /     z[mm]  \ 2
= L0x[mm] * \ | 1 + ( ( ------- )  - 1 ) * ( 1 - ------- )
             \|      \ \L0x[mm]/      /    \     zfx[mm] /
```

LSx  = a0x * azimBwidthAtSurface-fraction

```
                    cH20[mm/usec]    zfx[mm]
L0x[mm] = b[1] * ---------------- * --------    ( = b lambda f#)
                    freq[MHz]        a0x[mm]
```

3/

$$Ly(z, freq, ang)\,[mm] = L0y\,[mm] * \sqrt{1 + \left(\left(\frac{LSy\,[mm]}{L0y\,[mm]}\right)^2 - 1\right) * \left(1 - \frac{z\,[mm]}{Zfy\,[mm]}\right)^2}$$

```
LSy      = a0y * elevBwidthAtSurface-fraction c_sppa[1]*.V^2 = is modelled as piecewise linear in V^2
                 and is described by a few values pairs:
                 (Vn, Cn) n = 1 ... N
                 from the imaging spec.
                 (it is assumed that the C*V^2 curve goes through the origin)

This means C is interpolated like that:

C(V) * V^2 = alpha * Cn * Vn^2 + (1-alpha) * Cn+1 * Vn+1^2 where:  Vn < V <= Vn+1

Vn+1^2 - V^2
                  alpha = -------------
                          Vn+1^2 - Vn^2 or   C(V) = beta * Cn + (1-beta) * Cn+1

V~^2  - Vn^2                         Vn+1 * Vn
                 beta = -------------     where V~ =  ---------
                         Vn+1^2 - Vn^2                         V W3_pa_acoust[W] =
        aAvg(freq,cyc)[1] * W0_pa_elec[W] * 10^(-0.003 * freq[MHz] * z[mm])
W0_pa_elec[W] =
           1
          ---- * g(freq)[umho] * Asq_unsc_sum(apod,f#)[1] * V_pulse_rms^2[V^2]
          10^6 azimBwidthAtSurface-fraction (e-factor)   model param. from meas/IS
elevBwidthAtSurface-fraction (e-factor)   model param. from meas/IS b(freq, ang, apod)[1]                     model param. from meas/IS
a0x[mm]                                   azim aperture from ACQ
zfx[mm]                                   focus range from ACQ
freq[MHz]                                 -3dB center freq of output carrier freq
                                           from ACQ
a0y[mm]                                   elevational aperture from IS
L0y(freq, ang)[mm]                        elev min e-e beam width from meas/IS
Zfy(freq, ang)[mm]                        elev focus range from meas/IS
C_sppa_grid_val(freq,ang,ztx,apod)[1]     model param. from meas/IS
Vpp_sppa_grid(freq,ang,ztx,apod)[V]       model param. from meas/IS
aAvg(freq,gNumber)[1]                     model param. from meas/IS
g(freq)[umho]                             elec. conductance from IS
                                           (from xdcr group or thermal meas.)
Asq_unsc_sum(apod,f#)[1]                  apodization values squared and
                                           summed over apod profile of center
                                           line; calc by ACQ
```

3a

```
V_pulse_rms[V]                         ]   rms of xmt voltage over pulse
                                            for normalized apodization;
                                            calc by ACQ Combination of several xmt componenents: take maximum
------------------------------------------------------------------------

2) MI[1]:
   ======
Mechanical Index

MI[1] = maximum of
        over z

+-------------------------------------------------------------------
     _|       W.3_min_acoust[W] * rho[g/cm3] * c_H2O[mm/usec]    MHz
    _\|c_mi[1]* ------------------------------------------------ * ----
     \|           A_ee_beam[mm2] * freq[MHz]                     MPa2 c_mi[1] = model parameter similar to c_isppa

W.3_min_acoust[W] =
            aMax(freq,cyc)[1] * W0_min_elec[W] * 10^(-0.003*freq[MHz]*z[mm])
                          1
W0_min_elec[W]   = ---- g(freq)[umho] * Asq_unsc_sum(apod,f#) * V_min^2[V2]
                   10^6 aMax(freq,gNumber)[1]                  model param. from meas/IS g, Asq_unsc_sum(apod,f#), A_ee_beam: see above V_min(pulse shape)[V2]                 min of xmt voltage for normalized
                                       apod.
V_min = V_max = Vpp/2
Vpp                                    peak-to-peak of xmt voltage
rho = 1 g/cm3                          density of water; constant (1g/cm^3)
c_H2O = 1.5246 mm/usec                 speed of sound: constant (in water)

Combination of several xmt componenents: take maximum
------------------------------------------------------------------------

3) Ispta_t (starting with Sequoia software version 1.61, changed for 2.5):
   ======================================================================
                                /          W.3_rms_acoust[mW] \
Ispta_t[mW/cm2] = 100 * maximum ( c_sppa[1] * ---------------- )
                        over z  \          A_ispta(z)[mm2]    /

W.3_rms_acoust[mW]   =
         aAvg(freq)[1] * W0_rms_elec[mW] * 10^(-0.003*freq[MHz]*z[mm])

1
W0_rms_elec[mW]    = ---- g(freq)[umho] * Asq_scan_sum[1]*V_total_rms^2[V2]
                     1000

A_ispta at the surface (z=0):
```

33

$A\_ispta(z=0) = (\ Lx(z=0)\ [mm]\ +\ Res\text{-}box\text{-}size(z=0)\ [mm]\ )\ *\ Ly(z=0)\ [mm]$ (Note: With release 2.5 it was introduced to compute Ispta at the surface differently than for z > 0. For z=0 we went back to the pre 1.61 formulation)

A_ispta for z > 0:

$A\_ispta(z>0) = Ispta\ equivalent\ area = num\_lines * Lx * Ly\ /\ BOF$ $$\frac{1}{A\_ispta} = \frac{BOF}{num\_lines * Lx * Ly}$$

$$BOF = \begin{cases} \sqrt{1 + \dfrac{Lx * (num\_lines - 1)}{Res\text{-}box\text{-}size}} & \text{if } Lx < Res\text{-}box\text{-}size \\ num\_lines & \text{if } Lx >= Res\text{-}box\text{-}size \end{cases}$$

$$\frac{1}{A\_ispta} = \begin{cases} \dfrac{\sqrt{1 + \dfrac{Lx * (num\_lines - 1)}{Res\text{-}box\text{-}size}}}{num\text{-}lines * Lx * Ly} & \text{if } Lx < Res\text{-}box\text{-}size \\ \dfrac{1}{Lx * Ly} & \text{if } Lx >= Res\text{-}box\text{-}size \end{cases}$$

```
Lx(z) [mm], Ly(z) [mm]      for center line; see Isppa
Isppa[1]                    for center line; see Isppa Asq_scan_sum(apod,f#)    = apodization values squared, summend over
[1]                        apod profile and then averaged over the component's
                           firings in one frame; calc by ACQ
V_total_rms[V]             rms values of xmt-voltage over all time for normalized
                           apod; calc by ACQ
Res-box-size(z) [mm]       RES/PAN box dimension as fct of z; calc by ACQ
                           depends on start and end line and scan geometry
                           linear: r = (end_l-start_l+1) * line_spacing_in_mm
                           vector, curved lin, sector: r = arc
                           r = (end_l-start_l+1) * line_spacing * radius num_lines                  number of scan lines
``` derivation of A_ispta for z > 0
--------------------------------

$$Ispta = c * \frac{PII.3\_0 * FSC * BOF}{FT}$$

$W.3 = sum(PII.3) * Lx * Ly / FT$

34

```
sum(PII) = PII_0 * FSC * num_lines

PII.3_0 * FSC * num_lines * Lx * Ly         PII.3_0 * FSC * BOF
Ispta = c * ------------------------------------- = c * ---------------------
                      FT * A_ispta                               FT where
sum(PII) = sum over all firings in scan
FT       = frame-time
PII.3_0  = PII.3 of center line (or line at which Ispta is taken)
FSC      = flow sample count (total number of firings of each scan line
           including reverb, refire, "prime the pump" firings)
BOF      = beam overlap factor num-lines * Lx * Ly
=> BOF = ---------------------
                A_ispta num_lines * Lx * Ly
A_ispta = ---------------------
                 BOF Combination of several scan modes:
==================================
Ispta_t will be managed for each mode separately with possibly separate
limits. But the total Ispta is the sum over modes

--------------------------------------------------------------------------

# The following describes the now obsolete Ispta model:

# 3) Ispta_t (before Sequoia release 1.61):
#    ======================================
#                          /           W.3_rms_acoust[mW]  \
# Ispta_t[mW/cm2] = 100 * maximum ( c_sppa[1] * ------------------ )
#                          over z   \         A_ee_scan(z)[mm2] /

# W.3_rms_acoust[mW]  =
#           aAvg(freq)[1] * W0_rms_elec[mW] * 10^(-0.003*freq[MHz]*z[mm])
1
# W0_rms_elec[mW]     = ---- g(freq)[umho] * Asq_scan_sum[1]*V_total_rms^2[V2]
#                       1000

#                        /                                    \
# A_ee_scan[mm2]       = ( Lx(z)[mm] + Res-box-size(z)[mm] ) * Ly(z)[mm]
#                        \                                    /

# Lx(z)[mm], Ly(z)[mm]   for center line; see Isppa
# c_sppa[1]              for center line; see Isppa

# Asq_scan_sum(apod,f#) = apodization values squared, summend over
# [1]                     apod profile and then averaged over the component's
#                         firings in one frame; calc by ACQ
# V_total_rms[V]          rms values of xmt-voltage over all time for
#                         normalized
#                         apod; calc by ACQ
```

```
# Res-box-size(z) [mm]      S/PAN box dimension as fc   f z; calc by ACQ
#                           uepends on start and end line and scan geometry
#                           linear: r = (end_l-start_l+1) * line_spacing_in_mm
vector, curved lin, sector: r = arc
r = (end_l-start_l+1) * line_spacing * radius
```

---------------------------------------------------------------------

5) TI[1]
   =====

Thermal Index

```
--------------+-------------------------+-----------------------------------
              | Scanned:B,F             | Unscanned:M,F-M,PW,CW
--------------+-------------------------+-----------------------------------
TIS           | Eq A (surface)          | A_aper[mm2] >  100mm2: Eq B (depth)
              |                         | A_aper[mm2] <= 100mm2: Eq C (surface)

TIB           | Eq A (surface)          | Eq D (depth)

TIC           | Eq E (surface)          | Eq E (surface)
--------------+-------------------------+-----------------------------------
``` large aper: A_aper >  1cm^2
small aper: A_aper <= 1cm^2

Combining TI's:
===============================================================
let
    N    = N-th xmt component in the frame:
    SUM  = sum over N or appropriate subset of N
    MAX  = maximum over two terms
    X    = one of S, C, or B in general:
===========
TIX = MAX [ SUM(TIX_N_surface), SUM(TIX_N_depth) ]

in particular:
==============
TIS = MAX [ SUM(TIS_N_scanned) + SUM(TIS_N_unscanned_small_aper),
            SUM(TIS_N_unscanned_large_aper) ]

TISF := SUM(TIS_N_unscanned_large_aper) (definition; special addition)

TIB = MAX [ SUM(TIB_N_scanned), SUM(TIB_N_unscanned) ]

TIC = SUM(TIC_N)

or in other words:
==================

TIS = MAX [ SUM(TI_A) + SUM(TI_C), SUM(TI_B) ]

TIB = MAX [ SUM(TI_A), SUM(TI_D) ]

TIC = SUM(TI_E)

36

```
TISF := SUM(TI_B)

Formulae (surface):
===================
```

$$\text{Eq A: } TI\_A = \frac{W01[mW] * freq[MHz]}{210 * mW * MHz} \quad \text{(TIS or TIB; scanned; surface)}$$

$$\text{Eq C: } TI\_C = \frac{W0[mW] * freq[MHz]}{210 * mW * MHz} \quad \text{(TIS; unscanned; surface; small aper)}$$

$$\text{Eq E: } TI\_E = \frac{W0[mW] * (10mm)}{40 * Deq[mm] * mW} \quad \text{Note: the 10mm (original 1cm)} \quad \text{(TIC; scanned or not; surface)}$$

```
Formulae (depth):
=================
```

$$\text{Eq B: } TI\_B = \frac{freq[MHz]}{210*mW*MHz} * \max_{z>z\_bp} \left( \min(W.3(z)[mW], \ Ispta\_t(z)[mW/cm2]*1cm2) \right)$$

(TIS; unscanned; depth; large aper)

```
max-min determination:
======================
There are ONLY three cases to consider for the max over z > z_bp of min(W,I)

Case 1: W.3(z_bp) <= Ita.3(z_bp)    then max-min = W.3(z_bp)

Case 2: W.3(z_bp) >  Ita.3(z_bp) and there is at least one crossovers
        for z>z_bp:

let z_xo be the smallest of them then max-min = max [ W(z_xo), Ita.3(z_bp<z<z_xo) ]

Case 3: W.3(z_bp) >  Ita.3(z_bp) and there are NO crossovers for z>z_bp then max-min = max over z>z_bp of Ita.3(z)

summary:
```

| | |
|---|---|
| W.3(z_bp) <= Ita.3(z_bp) | W.3(z_bp) |
| W.3(z_bp) > Ita.3(z_bp) && W.3(z_xo)=Ita.3(z_xo) | max: Ita.3(z_bp<z<z_xo) |
| W.3(z_bp) > Ita.3(z_bp) && no x-overs | max Ita.3(z>z_bp) |

Eq D: TI_D = minimum of

*37*

$$\left| \frac{1}{50mW} * \sqrt{W.3(zB.3)[mW] * Ispta.3(zB.3)[mW/cm2] * cm2} \; , \; \frac{1}{4.4mW} \; W.3(zB.3)[mW] \right|_{+-}^{-+}$$

(TIB; unscanned; depth)

where:
======

```
W0[mW] = W0_rms_acoust[mW] = a(freq)[1] * W_rms_elec[mW]
                            (see above): avg. acoust power W01[mW] = W01_rms_acouts[mW] = a(freq)[1] * W01_rms_elec[mW]
         avg. acoust power through central 1cm of active aper 1
W01_rms_elec[mW] =   ----  g(freq)[umho] * A01[1] * V_total_rms^2[V2]
                     1000

W.3[mW] = W.3_rms_acoust[mW] = W0[mW] * 10^(-0.003 * freq[MHz] * z[mm])

Ispta_t[mW/cm2]  (see above)

A01[1]: 1cm-scanned_summed Apod: sum of apod. values squared over a 1cm
        long aperture (central 1cm); for the frame's N-th firing of the
        component square and sum the apod profile truncated by the central
        1cm; then average over all firings that compose this component's
        frame; calc by ACQ +----------------
                 |  4
Deq[mm] =   \    | --  * A_aper[mm]
             \   | PI z_bp[mm] = 1.5 * Deq[mm]

A_aper[mm2]: active aperture area
A_aper[mm2] = a0y[mm] * a0x_scanned_12db[mm]
a0x_scannned_active[mm]: size of scanned active aperture,
                    ie. aperture comprised
                    of all elts with V_rms >= -12dB max(V_rms);
                    calc by ACQ large aperture if A_aper >  1 cm^2=100 mm2
small aperture if A_aper <= 1 cm^2=100 mm2
zB.3 depth that maximizes W.3(z) * Ispta_t(z)
     or similarly, that maximizes Ispta derated with 0.6
``` summing of components and V-dependence:
=======================================
We sum the TI's at surface together and the ones at depth and
take the maximum of the two sums. For all TI terms that are
calculated from W we use V^2 dependence, for all TI terms that
are calculated from Ispta or sqrt(Ispta) we use the Isppa c-factor
or its sqrt.

```
Let:    _N  = denote the N-th component
         X  = S, B, or C
```

*38*

```
TIX = maximum ( TIX_surface, TIX_depth) for each X=S,B,C

Note: scaling with voltage: all W's are proportional to V^2
      whereas Ispta uses the Isppa-C-factor behavior

-------------------------------------------------------------------

6) Delta T: temperature rise at xdcr surface
   ==========================================
                 1
dT_skin/air[C] = ---- k_skin/air[C/W] * AperFct(SFSA)[1] * W0_rms_elec[mW]
                1000
k_skin/air: head capacity [C/W]; from thermal measurements; from IS
           for gel/air and gel/skin AperFct: aperture function
AperFct = min (AperFct_max, AperFct_slope * SFSA + AperFct_intercept)
AperFct_max, AperFct_slope, AperFct_intercept from IS;
                                         from thermal measurements SFSA: stationary fractional surface area
      measure of size of active scanned aperture SFSA = spanned aperture over all firings for component / max-xdcr-aperture
we approximate:
SFSA = a0x_scanned_12db[mm] / max_a0x_aperture[mm]

spanned means: all elements that are part of any firing during a frame
               for the component count for the spanned aperture 1
W0_rms_elec[mW]        = ---- g(freq)[umho] * Asq_scan_sum[1] * <V^2>_rms[V2]
                        1000
NOTE: the scan-factor (SF) that appears for the A128, is taken
      care of in the W0_rms calculation by ACQ
-------------------------------------------------------------------

Parameters for IEC1157:
=======================

Maximum underated rarefactional pressure: Pr.0:
===============================================

The maximum underated rarefactional Pressure in MPa.

This is essentially the same as the MI with two differences:
  - no division by frequency
  - no tissue deration Pr.0 = maximum of
       over z +-----------------------------------------------------------------
     |         W.0_min_acoust[W] * rho[g/cm3] * c_H2O[mm/usec]    1
  -\ | c_mi[1] * ---------------------------------------------- * ----
   \ |                        A_ee_beam[mm2]                      MPa2
```

39 c_mi[1] = MI-C-factor model parameter (same as for MI)

W.0_min_acoust[W] = aMax(freq,cyc)[1] * W0_min_elec[W]

$$W0\_min\_elec[W] = \frac{1}{10^6} g(freq)[umho] * Asq\_unsc\_sum(apod,f\#) * V\_min^2 [V2]$$

aMax(freq,gNumber)[1]         . acoust conversion model param. from .
                              meas/IS g[freq]                       electrical conductance in uMho
                              (model param)

Asq_unsc_sum(apod,f#), A_ee_beam: see above

V_min(pulse shape) [V2]       min of xmt voltage for normalized
                              apod.
V_min = V_max = Vpp/2
Vpp                           peak-to-peak of xmt voltage
rho = 1 g/cm3                 density of water; constant (1g/cm^3)
c_H2O = 1.5246 mm/usec        speed of sound: constant (in water)

Combination of several xmt componenents: take maximum

Ispta.0:
========

The underated spatial peak temporal average intensity

Same as Ispta without the tissue deration. Summed over modes and seq. foci.

W0:
===

Total (underated) average acoustic power

W0_rms_acoust[mW]    = aAvg(freq)[1] * W0_rms_elec[mW]

$$W0\_rms\_elec[mW] = \frac{1}{1000} g(freq)[umho] * Asq\_scan\_sum[1] * V\_total\_rms^2 [V2]$$

g(freq) [umho]       = elec. conductance from IS
                       (from xdcr group or thermal meas.)

Asq_scan_sum(apod,f#) = apodization values squared, summend over
[1]                    apod profile and then averaged over the component's
                       firings in one frame; calc by ACQ
V_total_rms[V]         rms values of xmt-voltage over all time for normalized
                       apod; calc by ACQ Iob:

40

```
====

Iob   = W0 / max_az_aper * max_el_aper * max(sfsa)

W0: underated average acoustic power (summed over modes and seq foci)

max_az_aper:   maximum azimuthal aperture
max_el_aper:   maximum elevational aperture
sfsa:          stationary fractional surface area (max over modes and seq foci)
max(sfsa):.    maximum over all modes and seq foci
```

---

```
Headrooms:
==========
In order to account for xdcr variability, the acoustic and thermal
parameters (MI, Isppa, Ispta, TI, delta-T) can be raised by some
dB headroom. This headroom can be frequency dependent and comes
from the imaging spec. There are two headrooms, one for acoustic
and one for thermal parameters, per (sample grid) frequency.

The online code will interpolate in frequency (in dB) or extrapolate
by repeating the last value (constant extrapolation) and then
use the resulting dB values to scale the acoustic conversions and
head capacity:

acoustDB:  acoustic headroom in dB interpolated to current output carrier
           frequency.
thermDB:   thermal headroom in dB interpolated to current output carrier
           frequency.
then
       aAvg_HR   = aAvg   * 10^(acoustDB/10)
       aMax_HR   = aMax   * 10^(acoustDB/10)
       k_skin_HR = k_skin * 10^(thermDB/10)
       k_air_HR  = k_air  * 10^(thermDB/10)

and these conversions and specific heat factors are used in the
above formulas.
```

---

```
Summary of Param from ISM:
==========================
b(freq, ang, apod) [1]              from meas/IS
axim E-factor[1]                    from meas/IS
a0y [mm]                            elevational aperture from IS
L0y(freq, ang) [mm]                 elev min e-e beam width from meas/IS
Zfy(freq, ang) [mm]                 elev focus range from meas/IS
elev E-factor[1]                    elev effective aperture from meas/IS
C0_sppa(freq,ang,ztx,apod) [1]      from meas/IS
V0_sppa(freq,ang,ztx,apod) [V]      from meas/IS
P+-sppa(freq,ang,ztx,apod) [1]      from meas/IS
aAvg(freq,gNumber) [1]              from meas/IS
aMax(freq,gNumber) [1]              from meas/IS
g(freq) [umho]                      elec. conductance from IS
scan geom info                      info to convert res/pan box extend
                                    from angle into mm; from IS
k_skin/air[C/W]                     head capacity from meas/IS
```

```
AperFct_slope[1]                              (thermal meas
AperFct_intercept[1]                          from meas/IS (thermal meas)
AperFct_max[1]                                from meas/IS (thermal meas)
Vpp_ref                                       from meas/IS (thermal meas)
tau                                           from Can's model
V_pulse_rms_ref                               from Can's model
electrical conductance[uMho]                  from Can's model
acoustic headroom[dB]                         from IS (val vs freq table)
thermal headroom[dB]                          from IS (val vs freq table)
                                              from IS (val vs freq table)

Summary of Param calculated by Acq:
===================================
freq[MHz]                                     output carrier freq (-3dB center freq)
zfx[mm]                                       tx focus range
usl angle[deg]                                us-line angle
apod type[1]                                  transmit apodization type
Vpp_ref[V]                                    reference peak-to-peak voltage for
                                              single elt with normalized apod
                                              (from Can's model)
Vpp                                           actual single elt Vpp for normal. apod
tau[usec]                                     single elt xmt e duration from Can's
                                              model
frame time[usec]
frame time allocated to each mode[usec]
scan area or res/pan-box size[mm]             extent in mm or angle
num_lines                                     number of scan lines aox[mm]                                       tx aperture
aox_scanned_12db[mm]                          size of scanned active aperture, ie.
                                              aperture comprised of all elts with
                                              V_rms >= -12dB max(V_rms) for a
                                              particular xmt component (in frame)

Asq_unsc_sum(apod,f#)[1]                      apodization values squared and
                                              summed over apod profile of center
                                              line; calc by ACQ
Asq_scan_sum(apod,f#,firings in frame)        apodization values squared and summend
[1]                                           over apod profile for each firing in
                                              frame and then average over those;
                                              calc by ACQ
A01(apod,f#,firings in frame)[1]              1cm-scanned_summed Apod: sum of apod.
                                              values squared over a 1cm long
                                              aperture (central 1cm); for the
                                              frame's N-th firing of the component
                                              square and sum the apod profile
                                              truncated by the central 1cm; then
                                              average over all firings that compose
                                              this component's frame.

Vpp[V]  (Vmax = Vpp/2)                        pulse peak to peak for normalized apod Vpp = Vpp_ref * absolute scale where Vpp_ref is calculated by Can's model (Vmax or Vpp replaces:                                                    )
     (<V^2>_min(pulse shape)                  min of xmt voltage^2             )
     (                                        for normalized apod              )
```

4ᵅ

V_pulse_rms [V]                              rms xmt voltag  averaged over pulse
                                             for one element with normalized apod V_pulse_rms = V_pulse_rms_ref * absolute-scale where:
          V_pulse_res_ref is computed offline by Can's model
          absolute-scale = Vpp / Vpp_ref V_total_rms [V]                              rms xmt voltage averaged over all time
                                             for one element with normalized apod.
                                             This includes all firings in a
                                             frame for this mode.
        so:
          V_total_rms^2 = V_pulse_rms^2 * tau * FSC * num_lines / frame-time
        where:
          V_pulse_rms see above
          tau is the pulse duration computed as risetime by Can's model
          FSC * num_lines means total number of firings for mode in frame Summary of Apodization sums:
============================
Let:
  Aij        = i-th element's apodization for the j-th scan line
  Xij        = i-th element's position for the j-th scan line
  Ni         = number of elts
  Nj         = number of scan lines aØx                =    max over i1, i2 of  | X_i1_j0 - X_i2_j0 | j0 = index of center line of scan area aØx_scanned_12db =      max over i1, i2 of  | X_i1 - X_i2 | where i1 and i2 denoted any of pair of elements
                                        /12\
                                      -(  -- )
                        with  Vrms (i) >= 10  \20/  * max over i Vrms(i)

Ni
                        ---
                        \                2
Asq_unsc_sum    =       >    | A_i_j0 |
                        /
                        ---
                        i=0
                        j0 = index of center line of scan area Nj    Ni
                                ----  ----
                        1   \     \              2
Asq_scan_sum    =      --   >     >   | A_i_j |
                        Nj  /     /
                            ----  ----
                            j=0   i=0

43

$$A01 \quad = \quad \max_{1cm} \frac{1}{N_j} \sum_{j=0}^{N_j} \sum_{i=0}^{N_i} \text{trunc\_1cm} \left( \left| A\_i\_j \right|^2 \right)$$
$$\text{lines} \quad \text{elts}$$

. where trunc_1cm (Aij^2) = 0    if i-th lies outside the 1 cm along aperture
                       = Aij^2  if i-th lies inside the 1cm along aperture NOTE: I have chosen to average over number of lines rather than just
      to sum.  This means that the Vrms would be over the time that any
      line is fired Vrms_total = Vrms_pulse * tau-pulse-length * FSC * num_lines / frame-time where FSC * num_lines really means total number of firings per frame
      (for this mode)

Even for A01 will be divide the sum by Nj, that is the total number of
      lines not just the ones that contribute to the sum.

```
Summary of Electrical Power Parameters:
============================================
W0_min_el  [W]  = 10^-6 * g(freq) [umho] * Asq_unsc_sum[1] * <V^2>_min[V2]
W0_pa_el   [W]  = 10^-6 * g(freq) [umho] * Asq_unsc_sum[1] * <V^2>_PA[V2]
W0_rms_el  [mW] = 10^-3 * g(freq) [umho] * Asq_scan_sum[1] * <V^2>_rms[V2]
W01_rms_el [mW] = 10^-3 * g(freq) [umho] * A01[1]          * <V^2>_rms[V2]
================================================================================ adutal management:
==================

1) short time constants (MI, Isppa_t)
=====================================
```

These are mode specific.  Managed in two phases, first estimate
some values for a "artificial" value of V (this includes the
parameters that tell how to "scale" the value for other V's)

$$\text{Isppa\_t}(V) = \text{Isppa\_t}(V0) * \frac{V^2}{V0^2} * \left( 1 - P+ * \left( 1 - \frac{V^2}{V0^2} \right) \right)$$

So for Isppa_t(V) is determined by 5 paramters:

Isppa_t(V)  = fct (Isppa_t(V0), V0, P+, P-, V)

MI(V)       = fct (MI_V0, V0, P+, P-, V)

So, we calculate the V that gives the Isppa_t at the limit.

```
2) long time constants (TI, DT, Ispta_t)
========================================
``` a) Ispta:

```
=========
managed in three steps:

1) Each mode is limited to a mode maximum value from IS
2) The total Ispta is limited to the sum limit from IS (FDA limit)
   by reducing each mode proportional to its value after step 1
3) Each mode is limited to the currently user selected Ispta limit b) TI and DT
============
all modes are calculated over whole frame and then summed according
to summing formulas 3) managing
=========== first calculate maximum short time voltage for each mode (either
limited acoustically or thermally)

based on this voltage each mode calculates Ispta and reduces voltage
if necessary to meet Ispta_limits.

TI and DT are calculated and V is reduced proportionally for each
mode to make DT below the limit.

Electrical limits are calculated and V is again reduced proportionally
if necessary.

Finally further reduction if the user has a lower limit on MI or Ispta
selected or has as dB reduction selected.

Questions/Notes:
================
- Note: peak apod not needed
- Note: MI evaluated at z_MI_max, not z_PII.3_max
- Note: rho * c: density/speed are water values
- Note: V^2 for normalized apod
- Note: Asq_scan_summed should be averaged over firings in frame
- Note: res-box-size is the arc for sector/vector/curved linear
- Note: c_sppa for Ispta_t
- Note: Ispta_t is using center line values for beam-area and c_sppa
- Note: currently just adding Ispta_t's - no optimization over z
        The opt could be used in verify or what do regulations say?
- Note: The factoring of W_rms into space and time reasonable even
        if both V_i and Apod_i change with i-th firing in frame
- Note: A01 is averaged over line firings, summed over each elt per line
        firing.
- Note: V dependence of TI: either V^2, c-factor or sqrt(c-factor)
- Note: CW should fall out
- Note: We will base the single line parameters on the broadside line
        Even if the broadside line lies outside the pan/res box ? AuxCW ?

single line firing parameters (per xmt component):
==================================================
Float    outputCarrierFreqMHz;    // Can's model
Float    usLineAngleDeg;
Float    xmtFocusMm;
Id       baseApodTypeId;
```

```
Float     xmtVppV;

Float     xmtApertureMm;            // arc length for curved linear
Float     xdcrCurvatureRadiusMm;    // infinite for linear stacks
  or
Float     xmtAperChordMm;           // = xmtApertureMm for linear stacks
                                    // = chord          for curved linear stack
                                    // or use radius of curvature instead
Float     elevApertureMm;

Float     refPulseVppV;             // Can's model
Float     refPulseRmsV;             // Can's model
Float     refPulseTauUSec;          // Can's model Float     electConductanceUMho;

Float     sumApodSquares;           // for the single line: sum over elements scanning parameters (per xmt component):
==========================================
Float     frameTimeUSec;            // only one (not per component)
Float     numFirings;
Float     linearResBoxSizeMm;       // for linear scan format
Float     angleResBoxSizeDeg;       // for sector,vector,curved-linear
Float     resRadiusOffsetMm;        // for sector,vector,curved-linear Float     sumSumApodSquares;        // Apod^2 summed over firings summed over elts
Float     trunc1CmSumSumApodSq;     // Apod^2 summed over firings summed over elts
                                    // truncated to max 1cm of xmt aperture Float     aperScanned12dbMm;        // scanned apert. w. Vrms within -12db of max approximations made:
=====================
1) negative voltage amplitude is approximated by 1/2 of the envelope peak-
   to-peak voltage
2) aperScanned12db is approximated by SFSA * max-aperture CW mode:
========
CW fits naturally into the model, it is not measured separately.
However, some input parameters are arbitrary as long as certain
relationships are preserved:

1) refPulseRmsV = 1/4 * sqrt(2) * Vpp
2) tau * Num-pulses-per-frame = frame-time * mode-frame-time-fraction where tau, Num.. and frame-time are arbitrary
```

What is claimed is:

1. For use with a medical diagnostic ultrasound imaging system operative to generate an ultrasound image and comprising a transducer operative to transmit an ultrasonic beam, a method for determining an acoustic output parameter of the transmitted ultrasonic beam in a user-selected region in the ultrasound image, the method comprising:

(a) transmitting an ultrasonic beam from a transducer of a medical diagnostic ultrasound imaging system;

(b) generating an ultrasound image with the medical diagnostic ultrasound imaging system;

(c) receiving, from a user, a selection of a region in the ultrasound image; and (d) determining an acoustic output parameter of the transmitted ultrasonic beam in the user-selected region.

2. The invention of claim 1 further comprising:

(e) providing an indication of the determined acoustic output parameter.

3. The invention of claim 2, wherein (e) comprises displaying the determined acoustic output parameter.

4. The invention of claim 1, wherein the user-selected region comprises a single point.

5. The invention of claim 1, wherein the user-selected region comprises a plurality of points and wherein (d) comprises determining a respective acoustic output parameter for each of the plurality of points.

6. The invention of claim 5, further comprising:

(e) providing an indication of the determined acoustic output parameters for the plurality of points.

7. The invention of claim 6 wherein (e) comprises providing an isobar representation of the determined acoustic output parameters for the plurality of points.

8. The invention of claim 6 wherein (e) comprises providing a map representation of the determined acoustic output parameters for the plurality of points.

9. The invention of claim 8 wherein (e) comprises providing a grayscale map representation of the determined acoustic output parameters for the plurality of points.

10. The invention of claim 8 wherein (e) comprises providing a color map representation of the determined acoustic output parameters for the plurality of points.

11. The invention of claim 5 further comprising:

(e) determining a distribution of the determined acoustic output parameters for the plurality of points.

12. The invention of claim 11 further comprising:

(f) providing an indication of the determined distribution of the determined acoustic output parameters for the plurality of points.

13. The invention of claim 12, wherein (f) comprises displaying the determined acoustic output parameters for the plurality of points.

14. The invention of claim 1 further comprising:

(e) achieving a specified acoustic output parameter of the transmitted ultrasonic beam in the user-selected region by automatically adjusting an operating parameter of the medical diagnostic ultrasound imaging system.

15. The invention of claim 1 further comprising:

(e) determining acoustic attenuation of the transmitted ultrasonic beam; and (f) correcting the determined acoustic output parameter for the determined acoustic attenuation.

16. The invention of claim 1, wherein the acoustic output parameter is determined using an acoustic model, and wherein the invention further comprises calibrating the acoustic model with an in vivo measurement of contrast agents with different non-linear response levels.

17. For use with a medical diagnostic ultrasound imaging system operative to generate an ultrasound image and comprising a transducer operative to transmit an ultrasonic beam, a method for achieving a specified acoustic output parameter of the transmitted ultrasonic beam in a selected region in the ultrasound image, the method comprising:

(a) transmitting an ultrasonic beam from a transducer of a medical diagnostic ultrasound imaging system;

(b) generating an ultrasound image with the medical diagnostic ultrasound imaging system;

(c) selecting a region in the ultrasound image; and (d) determining an acoustic output parameter of the transmitted ultrasonic beam in the selected region;

(e) achieving a specified acoustic output parameter of the transmitted ultrasonic beam in the selected region by automatically adjusting an operating parameter of the medical diagnostic ultrasound imaging system.

18. The invention of claim 17, wherein (c) comprises automatically selecting a region in the ultrasound image.

19. The invention of claim 17, wherein (c) comprises automatically selecting a region at a specified image depth in the ultrasound image.

20. The invention of claim 17, wherein (c) comprises automatically selecting a region at a transmit focus of the transmitted ultrasonic beam.

21. The invention of claim 17, wherein (c) comprises receiving, from a user, a selection of a region in the ultrasound image.

22. The invention of claim 17 further comprising:

(f) providing an indication of the achieved acoustic output parameter.

23. The invention of claim 22, wherein (f) comprises displaying the achieved acoustic output parameter.

24. The invention of claim 17, wherein the selected region comprises a single point.

25. The invention of claim 17, wherein the selected region comprises a plurality of points.

26. The invention of claim 17 further comprising:

(f) determining acoustic attenuation of the transmitted ultrasonic beam; and (g) correcting the determined acoustic output parameter for the determined acoustic attenuation.

27. The invention of claim 17, wherein the acoustic output parameter is determined using an acoustic model, and wherein the invention further comprises:

(f) calibrating the acoustic model with an in vivo measurement of contrast agents with different non-linear response levels.

28. For use with a medical diagnostic ultrasound imaging system operative to generate an ultrasound image and comprising a transducer operative to transmit an ultrasonic beam, a method for providing an indication of an acoustic output parameter of the transmitted ultrasonic beam in a selected region in the ultrasound image, the method comprising:

(a) transmitting an ultrasonic beam from a transducer of a medical diagnostic ultrasound imaging system;

(b) generating an ultrasound image with the medical diagnostic ultrasound imaging system;

(c) selecting a region in the ultrasound image, the selected region being different from a region containing a peak acoustic output parameter of the transmitted ultrasonic beam;

(d) determining an acoustic output parameter of the transmitted ultrasonic beam in the selected region; and (e) providing an indication of the determined acoustic output parameter.

29. The invention of claim 28, wherein (c) comprises automatically selecting a region in the ultrasound image.

30. The invention of claim 28, wherein (c) comprises automatically selecting a region at a specified image depth in the ultrasound image.

31. The invention of claim 28, wherein (c) comprises automatically selecting a region at a transmit focus of the transmitted ultrasonic beam.

32. The invention of claim 28, wherein (c) comprises receiving, from a user, a selection of a region in the ultrasound image.

33. The invention of claim 28, wherein (e) comprises displaying the determined acoustic output parameter.

34. The invention of claim 28, wherein the selected region comprises a single point.

35. The invention of claim 28, wherein the selected region comprises a plurality of points and wherein (d) comprises determining a respective acoustic output parameter for each of the plurality of points.

36. The invention of claim 35, wherein (e) comprises providing an indication of the determined acoustic output parameters for the plurality of points.

37. The invention of claim 35, wherein (e) comprises providing an isobar representation of the determined acoustic output parameters for the plurality of points.

38. The invention of claim 35, wherein (e) comprises providing a map representation of the determined acoustic output parameters for the plurality of points.

39. The invention of claim 38 wherein (e) comprises providing a grayscale map representation of the determined acoustic output parameters for the plurality of points.

40. The invention of claim 38 wherein (e) comprises providing a color map representation of the determined acoustic output parameters for the plurality of points.

41. The invention of claim 35 further comprising:
(f) determining a distribution of the determined acoustic output parameters for the plurality of points.

42. The invention of claim 41 further comprising:
(g) providing an indication of the determined distribution of the determined acoustic output parameters for the plurality of points.

43. The invention of claim 42, wherein (g) comprises displaying the determined acoustic output parameters for the plurality of points.

44. The invention of claim 28 further comprising:
(f) achieving a specified acoustic output parameter of the transmitted ultrasonic beam in the selected region by automatically adjusting an operating parameter of the medical diagnostic ultrasound imaging system.

45. The invention of claim 28 further comprising:
(f) determining acoustic attenuation of the transmitted ultrasonic beam; and
(g) correcting the determined acoustic output parameter for the determined acoustic attenuation.

46. The invention of claim 28, wherein the acoustic output parameter is determined using an acoustic model, and wherein the invention further comprises calibrating the acoustic model with an in vivo measurement of contrast agents with different non-linear response levels.

47. For use with a medical diagnostic ultrasound imaging system operative to generate an ultrasound image and comprising a transducer operative to transmit an ultrasonic beam, a method for providing an indication of a location of a region in the ultrasound image in which an acoustic output parameter of the transmitted ultrasonic beam is determined, the method comprising:
(a) transmitting an ultrasonic beam from a transducer of a medical diagnostic ultrasound imaging system;
(b) generating an ultrasound image with the medical diagnostic ultrasound imaging system;
(c) determining an acoustic output parameter of the transmitted ultrasonic beam in a region in the ultrasound image, the region being less than the entire ultrasound image;
(d) providing an indication of the determined acoustic output parameter; and
(e) providing an indication of a location of the region in the ultrasound image.

48. The invention of claim 47, wherein the acoustic output parameter comprises a peak acoustic output parameter and wherein the location comprises a location of the peak acoustic output parameter.

49. The invention of claim 47, wherein the acoustic output parameter comprises mechanical index and wherein the location comprises a location associated with the mechanical index.

50. The invention of claim 47, wherein (e) comprises providing a visual indicator on the ultrasound image at the region in the ultrasound image.

51. The invention of claim 47, wherein (e) comprise providing an indication of a range of the region.

52. The invention of claim 1, 17, or 28, wherein the region is selected from the group consisting of a point, at least one point in a line, at least one point enclosed by an arbitrary shape, and at least one point enclosed by a predefined shape.

53. The invention of claim 1, 17, or 28, further comprising displaying a mechanical index value of the transmitted ultrasonic beam.

54. The invention of claim 1, 17, 28, or 47, wherein the acoustic output parameter comprises an index of a thermal acoustic output of the transmitted ultrasonic beam.

55. The invention of claim 1, 17, 28, or 47, wherein the acoustic output parameter comprises an index of a mechanical acoustic output of the transmitted ultrasonic beam.

56. The invention of claim 1, 17, 28, or 47, wherein the acoustic output parameter is operative to affect contrast agent modification.

57. The invention of claim 1, 17, 28, or 47, wherein the acoustic output parameter is operative to affect a drug-carrying vessel.

58. The invention of claim 1, 17, 28, or 47, wherein the acoustic output parameter comprises acoustic power of the transmitted ultrasonic beam.

59. The invention of claim 1, 17, 28, or 47, wherein the acoustic output parameter comprises acoustic energy of the transmitted ultrasonic beam.

60. The invention of claim 1, 17, 28, or 47, wherein the acoustic output parameter comprises acoustic pressure of the transmitted ultrasonic beam.

* * * * *